(12) United States Patent
Pitkänen

(10) Patent No.: US 12,195,714 B2
(45) Date of Patent: Jan. 14, 2025

(54) BIOREACTORS FOR GROWING MICRO-ORGANISMS

(71) Applicant: Solar Foods Oyj, Vantaa (FI)

(72) Inventor: Juha-Pekka Pitkänen, Vantaa (FI)

(73) Assignee: Solar Foods Oyj, Vantaa (FI)

( * ) Notice: Subject to any disclaimer, the term of this patent is extended or adjusted under 35 U.S.C. 154(b) by 797 days.

(21) Appl. No.: 17/413,656

(22) PCT Filed: Dec. 20, 2019

(86) PCT No.: PCT/FI2019/050920
§ 371 (c)(1),
(2) Date: Jun. 14, 2021

(87) PCT Pub. No.: WO2020/148480
PCT Pub. Date: Jul. 23, 2020

(65) Prior Publication Data
US 2022/0073856 A1 Mar. 10, 2022

(30) Foreign Application Priority Data

Jan. 14, 2019 (FI) .................. 20195020

(51) Int. Cl.
*C12M 1/06* (2006.01)
*C12M 1/00* (2006.01)
(Continued)

(52) U.S. Cl.
CPC ............ *C12M 27/02* (2013.01); *C12M 27/24* (2013.01); *C12M 29/06* (2013.01); *C12M 41/00* (2013.01)

(58) Field of Classification Search
CPC ...... C12M 27/02; C12M 27/24; C12M 29/06; C12M 41/00; C12M 41/32; C12M 1/08; C12M 27/20
See application file for complete search history.

(56) References Cited

U.S. PATENT DOCUMENTS 3,962,042 A 6/1976 Malick
5,248,613 A * 9/1993 Roubicek ............... C12M 41/02
210/219

(Continued)

FOREIGN PATENT DOCUMENTS

CN 2608509 Y 3/2004
CN 1766080 A * 5/2006 ............ C12M 27/02

(Continued)

OTHER PUBLICATIONS

Translation of CN-201135867-Y, Liu, Yong-Ding, Oct. 22, 2008 (Year: 2008).*

(Continued)

Primary Examiner — Samuel P Siefke
Assistant Examiner — Henry H Nguyen
(74) Attorney, Agent, or Firm — Ziegler IP Law Group LLC.

(57) ABSTRACT

A bioreactor for growing micro-organisms, has a reaction chamber containing a reaction mixture with a reaction medium and micro-organisms. A draft tube is arranged inside the reaction chamber, which has a gas inlet, an inlet for the reaction mixture at its first end, and an outlet for the reaction mixture at its second end. The bioreactor includes means for generating flow of the reaction mixture within the reaction chamber and a first blade structure arranged inside the reaction chamber, surrounding the draft tube. The first blade structure has blades arranged at, at least one of an angle $\alpha_1$ with respect to a direction defined by the height of the reaction chamber, or an angle $\alpha_2$ with respect to a direction defined by the height of the reaction chamber. The bioreactor also includes an inlet for reaction medium and an outlet for withdrawing medium with grown micro-organisms.

20 Claims, 9 Drawing Sheets

(51) Int. Cl.
  *C12M 1/08* (2006.01)
  *C12M 1/34* (2006.01)

(56) References Cited

U.S. PATENT DOCUMENTS

| | | |
|---|---|---|
| 5,660,977 A | 8/1997 | Flores-Cotera et al. |
| 2003/0106856 A1 | 6/2003 | Choe |
| 2008/0118946 A1 | 5/2008 | Fabiyi et al. |
| 2008/0206734 A1* | 8/2008 | Asgari ............... C12M 27/20 435/383 |
| 2010/0034050 A1 | 2/2010 | Erb et al. |
| 2010/0035342 A1 | 2/2010 | Cheng et al. |
| 2015/0259639 A1 | 9/2015 | Silverman et al. |
| 2018/0119083 A1 | 5/2018 | Zheng et al. |
| 2018/0187139 A1* | 7/2018 | Patel ............... C12M 23/40 |

FOREIGN PATENT DOCUMENTS

| | | | | |
|---|---|---|---|---|
| CN | 201135867 Y | * | 10/2008 | ............ C12M 27/02 |
| CN | 201330250 Y | | 10/2009 | |
| CN | 204058559 U | | 12/2014 | |
| CN | 204918587 U | | 12/2015 | |
| CN | 106916727 A | | 7/2017 | |
| CN | 108949514 A | * | 12/2018 | ............ C12M 27/02 |
| CN | 109196086 A | | 1/2019 | |
| EP | 0057659 A2 | | 8/1982 | |
| EP | 0191356 A1 | | 8/1986 | |
| EP | 2126036 A1 | | 12/2009 | |
| GB | 1417487 A | | 12/1975 | |
| JP | H03103171 A | | 4/1991 | |
| JP | 2004089759 A | | 3/2004 | |
| JP | 2011530290 A | | 12/2011 | |
| WO | 2018076414 A1 | | 5/2018 | |

OTHER PUBLICATIONS

Translation of CN-1766080-A, Tan, Wen-song, May 3, 2006 (Year: 2006).*
Translation of CN 108949514A, Zhang, Chao, Dec. 7, 2018 (Year: 2018).*
China National Intellectual Property Administration, First Office Action and Notice of First Examination Opinion, Application No. 201980087890.5, Dated Nov. 17, 2023, 13 pages.
Japan Patent Office, Decision to Grant a Patent, Application No. 2021-537978, Mailed Nov. 8, 2022, 3 pages.
Finnish Patent and Registration Office, Search Report, Application No. 20195020, mailed Aug. 9, 2019, 2 pages.
International Search Report and Written Opinion of the International Searching Authority, Application No. PCT/FI2019/050920, mailed Apr. 17, 2020, 13 pages.

* cited by examiner

BIOREACTORS FOR GROWING MICRO-ORGANISMS

TECHNICAL FIELD

The present disclosure relates generally to bioreactors and more specifically to bioreactors for growing micro-organisms.

BACKGROUND

Micro-organisms play a vital role in supporting and improving quality of life of humans and animals. Furthermore, micro-organisms are regularly used to support production of innumerable food products and pharmaceutical compounds, to aid physiological processes, to treat sewage and wastewaters and in several manufacturing and research processes. Therefore, micro-organisms grown using processes adhering to good manufacturing practices in controlled physical and chemical environments are required in multiple fields. Typically, bioreactors are employed to ensure such controlled environments for proper growth of the micro-organisms.

Generally, micro-organisms require optimally balanced environmental conditions such as mixture of nutrients, gases, heat, pH and pressure for proper growth in a bioreactor. For several processes such as gas fermentations, micro-organisms are grown in a liquid phase. Typically, such liquid mainly comprises water and nutrients, and are further provided with gases such as hydrogen ($H_2$), oxygen ($O_2$) and carbon dioxide ($CO_2$). However, a substantial amount of energy is used to dissolve the aforesaid gases in the liquid. Moreover, a portion of the gases may be left undissolved. Subsequently, such portion of gases are not used by the micro-organisms and therefore, energy efficiency for utilization of gases is negatively affected.

Typically, the gases are pumped with a defined pressure from a bottom of the bioreactor, into the liquid contained in the bioreactor. Subsequently, gases rise from the bottom of the bioreactor to a top of the bioreactor. Furthermore, the gases are generally used by the micro-organisms in a time the gases rise from the bottom to the top. Therefore, the time taken by the gases to rise from the bottom to the top needs to be maximized, owing to proportional relation between the time taken by the gases to rise from the bottom to the top and probability of micro-organisms being able to use the gas. Furthermore, the gases that are pumped into the bottom of the bioreactor form gas bubbles inside the liquid. Subsequently, size of the gas bubbles has to be minimized in order to maximize the area in which gas molecules can be taken up by the micro-organism for use thereof.

Conventionally, bioreactors include gas spargers implemented at the bottom of a reaction chamber for sparging the gases into the liquid and subsequently, using Rushton turbines (namely, radial flow impellers) to break the gas bubbles. However, the use of Rushton turbines in bioreactors results in formation of liquid free zones (also referred to as cavitation) in the reaction chamber and may decrease energy efficiency of the turbine. Furthermore, in order to increase residence time of gases in the liquid, different geometrical arrangements such as U-tube arrangement are employed. Specifically, in the U-tube arrangement, the liquid is circulated through a large U-shaped pipe using a pump. Additionally, the U-tube arrangement may comprise using static mixers for mixing of the liquid. Moreover, implementations of the bioreactor may include various airlift reactor designs. In such airlift reactor designs, the gases rising through the liquid move the liquid up a riser section of the reactor; subsequently, the gases separate from the liquid and the liquid without the gas bubbles returns through a downcorner section of the reactor. In an implementation of a bioreactor design by Outotec Oyj named OKTOP®, a draft tube and a pumping agitator connected to a mixer motor are employed. In such implementation, liquid is moved using the pumping agitator in the draft tube. Such pumping, mixing and sparging systems ensure proper mixing of gases in liquid in the bioreactors. However, these systems can only support growth of slow growing cultures such as mammalian cells but do not support intensive microbial growth.

Therefore, in light of the foregoing discussion, there exists a need to overcome drawbacks associated with conventional bioreactor designs.

SUMMARY

The present disclosure seeks to provide a bioreactor for growing micro-organisms. The present disclosure seeks to provide a solution to the existing problem of low dissolution and short residence time of gases in reaction mixture inside a bioreactor. An aim of the present disclosure is to provide a solution that overcomes at least partially the problems encountered in prior art, and provides an efficient and robust design for a bioreactor that achieves higher residence time of gases in the reaction mixture for optimal growth of micro-organisms.

In one aspect, an embodiment of the present disclosure provides a bioreactor for growing micro-organisms, comprising a reaction chamber for containing a reaction mixture comprising a reaction medium and micro-organisms, said reaction chamber having a first end, a second end, an inner height $H_r$ defined by the distance between the inner surface at first end and the inner surface at the second end, and an inner diameter $D_r$, and comprising
  a draft tube arranged inside the reaction chamber, having
    a first end, a second end and a side wall connecting the first end to the second end,
    an inner diameter $D_d$, wherein $D_d$ is smaller than $D_r$,
    a height $H_d$ defined by the distance between the first end and the second end, wherein $H_d$ is smaller than $H_r$,
    at least one gas inlet,
    an inlet for the reaction mixture at its first end, and
    an outlet for the reaction mixture at its second end;
  means for generating flow of the reaction mixture within the reaction chamber;
  at least a first blade structure arranged inside the reaction chamber, surrounding the draft tube, wherein the at least first blade structure comprises a plurality of blades arranged at, at least one of:
    an angle $\alpha_1$ with respect to a direction defined by the height of the reaction chamber, the angle $\alpha_1$ being 20-40°, or
    an angle $\alpha_2$ with respect to a direction defined by the height of the reaction chamber, the angle $\alpha_2$ being 320-340°;
  at least one inlet for reaction medium; and
  at least one outlet for withdrawing medium with grown micro-organisms.

Embodiments of the present disclosure substantially eliminate or at least partially address the aforementioned problems in the prior art, and enable production of gas bubbles of small size to provide larger surface area for binding of liquid, thereby ensuring proper mixing of the reaction mixture with gases.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1:
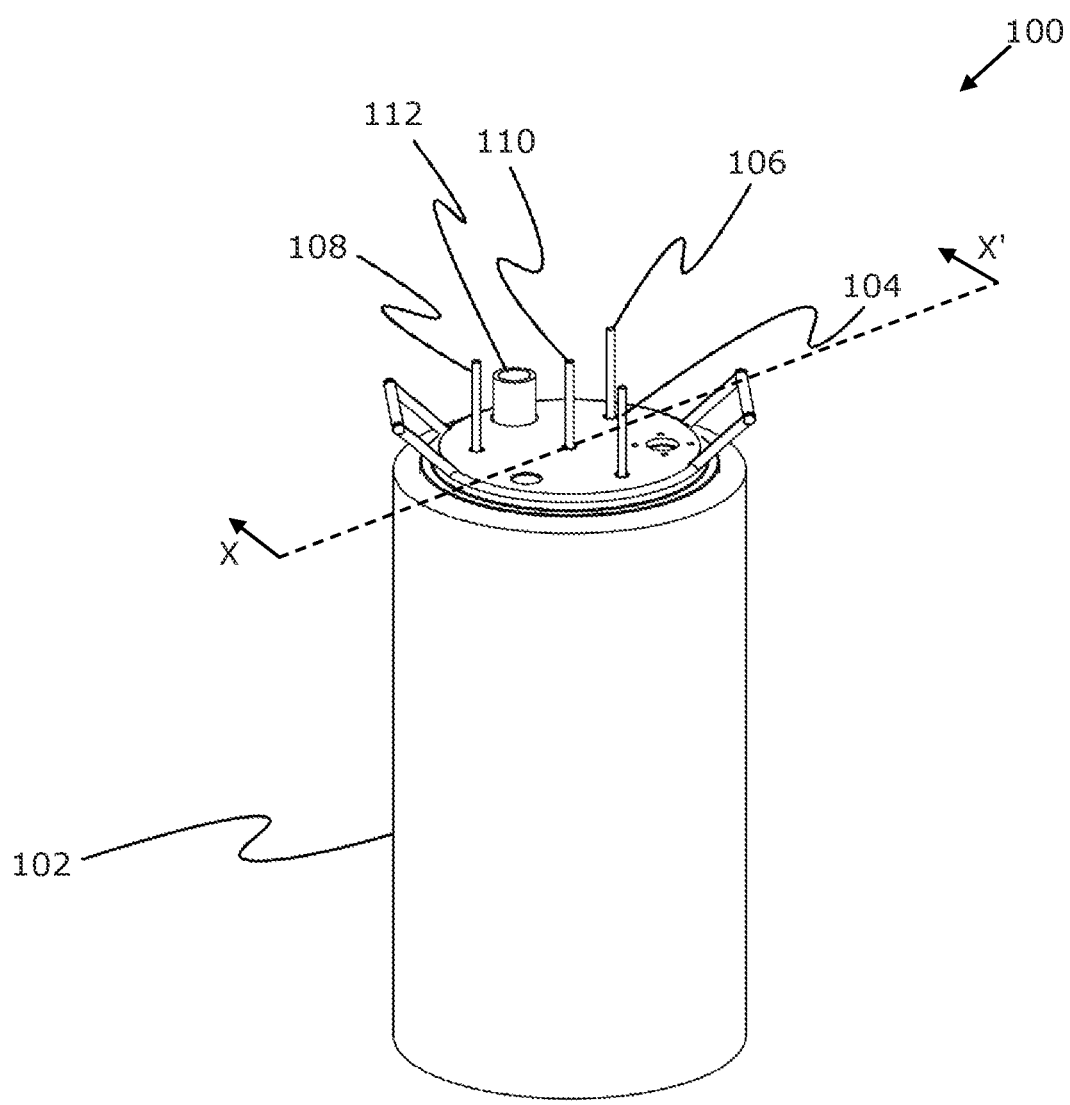
FIG. 1 is a schematic illustration of a bioreactor for growing micro-organisms, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a bioreactor for growing micro-organisms, comprising a reaction chamber for containing a reaction mixture comprising a reaction medium and micro-organisms, said reaction chamber having a first end, a second end, an inner height $H_r$ defined by the distance between the inner surface at first end and the inner surface at the second end, and an inner diameter $D_r$, and comprising a draft tube arranged inside the reaction chamber, having
  a first end, a second end and a side wall connecting the first end to the second end,
  an inner diameter $D_d$, wherein $D_d$ is smaller than $D_r$,
  a height $H_d$ defined by the distance between the first end and the second end, wherein $H_d$ is smaller than $H_r$,
  at least one gas inlet,
  an inlet for the reaction mixture at its first end, and
  an outlet for the reaction mixture at its second end;
means for generating flow of the reaction mixture within the reaction chamber;
at least a first blade structure arranged inside the reaction chamber, surrounding the draft tube, wherein the at least first blade structure comprises a plurality of blades arranged at, at least one of:
  an angle $\alpha_1$ with respect to a direction defined by the height of the reaction chamber, the angle $\alpha_1$ being 20-40°, or
  an angle $\alpha_2$ with respect to a direction defined by the height of the reaction chamber, the angle $\alpha_2$ being 320-340';
at least one inlet for reaction medium; and
at least one outlet for withdrawing medium with grown micro-organisms.

The present disclosure provides the aforementioned bioreactor for growing micro-organisms. The micro-organisms find various applications, including in food, pharmaceutical, cosmetics, and so forth, when grown under good manufacturing practices (GMP). The bioreactor ensures efficient use of gases and nutrients by the micro-organisms for optimal growth thereof. The bioreactor of the present disclosure enables longer residence time for gas and liquid mixture by decreasing the size of the gas bubbles provided into the liquid phase and generating a flow of the reaction mixture, comprising liquid, nutrients and micro-organisms, evenly throughout the reaction chamber of the bioreactor. In this regard, the bioreactor employs at least one blade structure, preferably a plurality of blade structures, arranged at different locations within the bioreactor (when several blade structures are used) for breaking the larger gas bubbles, mixing the gas bubbles with the reaction mixture and generating flow of the reaction mixture within the reaction chamber. Beneficially, the blade structure comprises a plurality of blades, arranged at an angle with respect to the height of the bioreactor, to rotate the reaction mixture in different directions, clockwise and counter-clockwise, for efficient mixing of gas and liquid phase of reaction mixture. Additionally, beneficially, the bioreactor provides efficient withdrawal of micro-organisms upon growth for providing an overall energy efficient bioreactor for growing micro-organisms.

Throughout the present disclosure, the term "bioreactor" refers to a vessel intended for biological and/or biochemical reactions required for culturing cells, growing micro-organisms, and production of biomolecules of pharmaceutical interest therefrom, under defined and controlled physical and chemical conditions. The biomolecules of pharmaceutical interest are selected from a group comprising, but not limited to, vaccines, drugs, hormones, enzymes, antibodies, biopharmaceuticals, plasmid DNA, viruses, phage, proteins, peptides, and lipids, grown using processes adhering to good manufacturing practices under good manufacturing practice (GMP) conditions. The bioreactor may have a shape, for example cylindrical, conical, cuboidal or cubical. Furthermore, volume of the bioreactor is selected depending upon its use and may be for example 10 litres, 100 litres, 200 litres, 1000 litres, 5000 litres, 10000 litres, 20000 litres, 50000 litres, 100000 litres or 200000 litres. The bioreactor may be fabricated of a material that is inert to the contents of the bioreactor. In an example, the material used for fabrication may be stainless steel (for example type 304, 316 or 316L), other suitable metals or alloys, glass material, fibres, ceramic, plastic materials and/or combinations thereof. Moreover, the fabrication material is typically waterproof and strong enough to withstand abrasive effects of various biological, biochemical and/or mechanical processes, such as micro-organism concentrations, biomass productions, agitation forces, aeration forces, operating pressures, temperatures and so forth.

In the present description, by height and diameter are meant inner height and inner diameter, respectively, even if not specified, unless the part referred to does not have one or both ends, i.e. the inner height is the same as the outer height. By inner height it is meant the distance between the two ends of the part, measured inside, while inner diameter is the distance between the inner surfaces of the side walls. When a non-cylindrical part is used, the inner diameter denotes the largest dimension perpendicular to the height direction.

The bioreactor for growing micro-organisms comprises a reaction chamber for containing a reaction mixture comprising a reaction medium and micro-organisms. The reaction chamber is a vessel, inside the bioreactor, in which the biological and/or biochemical reactions are carried out. Furthermore, the reaction chamber has a first end, a second end, an inner height $H_r$ defined by the distance between the inner surface at first end and the inner surface at the second end, and an inner diameter $D_r$. According to an embodiment, the reaction chamber is cylindrical in shape, with a first end, i.e. top surface, and a second end, i.e. bottom surface. Optionally, the inner height $H_r$ of the reaction chamber, i.e. the distance between the inner surface at first end and the inner surface at the second end, may be in the range of 200-550 millimetre, preferably 300-500 millimetre, more preferably 340-410 millimetre. The inner height $H_r$ may be for example from 200, 210, 220, 230, 240, 250, 260, 270, 280, 290, 300, 310, 320, 330, 340, 350, 360, 370, 380, 390, 400, 410 or 420 mm up to 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540 or 550 mm. Optionally, the inner diameter $D_r$ of the reaction chamber, i.e. the distance between the inner surfaces of the side walls, may be in the range of 120-350 millimetre, preferably 170-300 millimetre, more preferably 220-260 millimetre. The inner diameter $D_r$ may thus be for example from 120, 130, 140, 150, 160, 170, 180, 190, 200, 210, 220, 230, 240, 250, 260, 270, 280, 290 or 300 mm up to 140, 150, 160, 170, 180, 190, 200, 210, 220, 230, 240, 250, 260, 270, 280, 290, 300, 310, 320, 330, 340 or 350 mm. For larger reaction chambers, the dimensions are naturally increased proportionally.

Throughout the present disclosure, the term "reaction mixture" refers to constituents inside the reaction chamber, employed for growth of micro-organisms. The reaction mixture comprises a reaction medium and micro-organisms. The reaction medium includes a liquid phase with or without nutrients and serves as a nutrient and growth medium for micro-organisms. The liquid phase may be selected from a group comprising water, water purified using, for example, reverse osmosis or distillation, sea water, brackish water, recycled process waters such as dairy run-off, saline media, and/or combinations thereof. The liquid phase may comprise added nutrients, including carbon, magnesium, potassium, phosphorus, sulphur, iron, zinc, manganese, nitrogen (for example in the form of ammonia, urea, nitrate, nitrite, amino acids, proteins (soluble, insoluble or hydrolysed)), animal by-products, dairy wastes, yeast, fatty acids, alcohols, polysaccharides, minerals, vitamins, growth factors, acids, bases, antibiotics, anti-foam agents, surfactants and the like.

It will be appreciated that the reaction mixture comprises an inoculum of micro-organisms that work as starting material for the generation of more micro-organisms under optimal growth conditions. Throughout the present disclosure, the term "micro-organism" refers to algae, bacteria, cyanobacteria, yeast, fungi, archaea and the like. The bioreactor provides for defined and controlled physiological conditions required for the growth of micro-organisms. Furthermore, the bioreactor may be used to culture eukaryotic cells, including plant cells, fungus, hybridoma cell lines and so forth. Initially, the bioreactor is seeded with a volume of inoculum from an aseptically maintained microbial culture. The micro-organisms are then allowed to grow in an environment for a period of time to achieve an optimum growth, pertaining to biomass or by-product of the microbial growth, to be subsequently harvested for later use. Optionally, the reaction mixture in the reaction chamber ranges from 0.5 to 20% of the volume of the reaction chamber. Optionally, the reaction mixture is prepared outside the bioreactor, such as in a sterile shake flask, under aseptic conditions, and then transferred to reaction chamber under aseptic conditions.

The bioreactor comprises a draft tube arranged inside the reaction chamber. The term "draft tube" as used herein refers to a conduit installed inside the reaction chamber for channeling liquid phase. Moreover, the draft tube improves circulation of the liquid phase, reduces bubble coalescence, and increases mixing efficiency of gases in liquid phase throughout the reaction chamber. The draft tube has a first end, a second end and a side wall connecting the first end to the second end. The first end pertains to a top or upper end of the draft tube, the second end pertains to a bottom end of the draft tube, and the side wall connects the first end and the second end of the draft tube. Preferably, the first end and the second end of the draft tube are open, giving a hollow cylindrical shape of the draft tube. Optionally, the draft tube may be fabricated from stainless steel (for example type 304, 316 or 316L), other suitable metals or alloys, glass material, fibres, ceramic, plastic materials and/or combinations thereof. Moreover, the fabrication material is typically waterproof and strong enough to withstand abrasive effects of various biological, biochemical and/or mechanical processes, such as micro-organism concentration, biomass production, pressure, agitation forces, aeration forces, temperature and the like.

The draft tube has an inner diameter $D_d$, wherein $D_d$ is smaller than $D_r$, and a height $H_d$ defined by the distance between the first end and the second end, wherein $H_d$ is smaller than $H_r$. It will be appreciated that the inner diameter $D_d$ and height $H_d$ of the draft tube are smaller than the inner diameter $D_r$ and inner height $H_r$ of the reaction chamber as the draft tube is enclosed within the reaction chamber. Optionally, the inner diameter $D_d$ of the draft tube may be in the range of 50-250 millimetre, preferably 70-180 millimetre, more preferably 90-130 millimetre. The inner diameter $D_r$ may thus be for example from 50, 60, 70, 80, 90, 100, 110, 120, 130, 140, 150, 160, 170, 180, 190 or 200 mm up to 80, 90, 100, 110, 120, 130, 140, 150, 160, 170, 180, 190, 200, 210, 220, 230, 240 or 250 mm. For larger reaction chambers, the dimensions are increased accordingly.

According to an embodiment, the height $H_d$ of the draft tube may be in a range of 150-400 millimetre, optionally 200-350 millimetre, more optionally 250-300 millimetre. For example, the height $H_d$ of the draft tube may be from 150, 160, 170, 180, 190 200, 210, 220, 230, 240, 250, 260, 270, 280, 290, 300, 310, 320, 330, 340, 350, 360 or 370 mm up to 180, 190 200, 210, 220, 230, 240, 250, 260, 270, 280, 290, 300, 310, 320, 330, 340, 350, 360, 370, 380, 390 or 400 mm. Again, for larger reaction chambers, these dimensions are scaled up accordingly.

According to an embodiment, the inner diameter $D_d$ of the draft tube is 111 millimetres and the inner diameter $D_r$ of the reaction chamber is 240 millimetres, thus the cross-sectional area of the draft tube is 21% of the cross-sectional area of the reaction chamber. This ratio could be for example 15-50%. The height $H_d$ of the draft tube is 275 millimetres, while the liquid height of the reaction chamber is 350 millimetres. In this case, the liquid level would be situated approximatively at a height above the draft tube, which height is half of the radius of the draft tube (about 27 millimetres), and clearance below the draft tube would be about 75% of the radius of the draft tube.

The draft tube further comprises at least one gas inlet. Optionally, the gas flows into the at least one gas inlet from a source of gas that stores gas under pressure. The gas may be air, oxygen, carbon dioxide, carbon monoxide, nitrogen, hydrogen, inert gases, oxides of nitrogen, methane, and so forth. More optionally, the gas may be used in a compressed state, and may be sparged into the reaction mixture. Furthermore, velocity of flow of gas to the at least one gas inlet is preferably controlled by a controller arrangement well known in the art. The controller arrangement regulates the velocity of flow of gas to achieve a desired velocity of flow of gas to the at least one gas inlet and subsequently to the draft tube. Optionally, the flowrate of gas may be in a range of 0.1 to 2 volume/minute. Optionally, the at least one gas inlet is provided on the side wall of the draft tube. The at least one gas inlet supplies gas to the inside of the draft tube through at least one connection opening, corresponding to the at least one gas inlet. Specifically, the ends of the at least one gas inlet are open and each connected through a connector to a respective connection opening in the draft tube. In an embodiment, the rate of flow of the reaction mixture may be in a range of 0.1 to 2 volume/minute. For example, if the volume of the reaction mixture in the bioreactor is 15 litres, the flow rate could be 15 litres/minute. This would lead to a flow velocity of 2.5 cm/s inside the draft tube.

Optionally, the at least one gas inlet comprises a nozzle comprising a number of openings for creating gas bubbles. The nozzle, for example a sparger, serves as a protrusion at the end of the at least one gas inlet, and comprises a number of openings, such as small holes, to disperse the at least one gas as gas bubbles into liquid. Specifically, the at least one gas is sparged in the lower parts of the draft tube, i.e. area between the first end and second end of the draft tube, through the connection openings therein. The gas sparged through the number of openings of the nozzle results in a combination of small and large gas bubbles. The diameter of the openings in the nozzle can be for example 0.5-200 μm, preferably 1-30 μm, more preferably 3-10 μm. In an embodiment, the shape of gas bubbles may any of tubular, spherical, hemispherical, ellipsoidal, semi-ellipsoidal and/or a combination thereof. The diameter may be for example from 0.5, 1, 2, 3, 5, 7, 10, 15, 20, 25, 30, 35, 40, 45, 50, 55, 60, 65, 70, 75, 80, 85, 90, 95, 100, 105, 110, 115, 120, 125 or 130 μm up to 1, 2, 3, 5, 7, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 μm.

Throughout the present disclosure, the term "sparge", "sparged" or "sparging" refers to a process of injecting a gas into a liquid phase by employing a sparger (or a diffuser or a nozzle). Sparging may be used to dissolve a gas into liquid, such as in aeration and carbonation, for further reaction in applications such as fermentation, ozonation, oxidation, hydrogenation and so forth. Alternatively, sparging may be used to remove contaminants from the liquid phase, such as in stripping applications and so forth. Generally, spargers are manufactured in different types, sizes, configurations and using fabrication materials. Spargers may be fabricated from different materials selected from a group of stainless steel, other suitable metals or alloys, glass material, fibres, ceramic, plastic materials and/or combinations thereof. Furthermore, the choice of spargers is further governed by the type of culture process, i.e. continuous or batch, velocity of flow of gas, volume of the reaction chamber, abrasive effects of various biological, biochemical and/or mechanical processes, such as agitation forces, aeration forces, operating pressure, temperature and so forth.

Optionally, the draft tube comprises at least two gas inlets, further optionally provided on the side wall of the draft tube. The at least two gas inlets may be provided to supply each of at least one gas selected from a group of oxygen, carbon dioxide, carbon monoxide, nitrogen, hydrogen, inert gases, oxides of nitrogen, methane and the like. In an example, a first gas inlet supplies a first gas, such as for example hydrogen and a second gas inlet supplies a second gas, such as for example oxygen. Alternatively, a mixture of gases may be supplied through any or both of the at least two gas inlets. Optionally, the two gas inlets are arranged diametrically opposed and at a same distance from the first end of the draft tube. It will be appreciated that the diametrically opposite arrangement and same distance from the first end of the draft tube ensures an even distribution of gas bubbles over the entire cross-section of the draft tube. Specifically, the protrusions of the two gas inlets sparges corresponding gases into the liquid phase inside the draft tube from each of the two openings on the side wall of the draft tube, while at the same time, producing an upward flow of the gas bubbles in the draft tube. Moreover, the same distance from the first end of the draft tube also ensures equal mixing of the at least two gases, without leaving a scope for the liquid phase to get saturated with only the first type of gas sparged therein.

Optionally, the draft tube comprises at least three gas inlets, again optionally provided on the side wall of the draft tube, arranged circumferentially equidistantly and at a same distance from the first end of the draft tube. The at least three gas inlets may be provided to supply each of at least one gas selected from a group of oxygen, carbon dioxide, carbon monoxide, nitrogen, hydrogen, inert gases, oxides of nitrogen, methane, and the like. In an example, a first gas inlet supplies a first gas, such as for example hydrogen, a second gas inlet supplies a second gas, such as for example oxygen, a third gas inlet supplies a third gas, such as for example carbon dioxide, and so forth. Alternatively, a mixture of gases may be supplied through any or all of the at least one gas inlet. Optionally, the three gas inlets are arranged circumferentially equidistantly and at a same distance from the first end of the draft tube. It will be appreciated that the circumferentially equidistant arrangement and same distance from the first end of the draft tube ensures an even distribution of gas bubbles over the entire cross-section of the draft tube. Specifically, the protrusions of the at least three gas inlets sparges corresponding gases into the liquid phase inside the draft tube from each of the three openings on the side wall of the draft tube, while at the same time producing an upward flow of the gas bubbles in the draft tube. Moreover, the same distance from the first end of the draft tube also ensures equal mixing of the at least three gases, without leaving a scope for the liquid phase to get saturated with only the first type of gas sparged therein.

Alternatively, the at least one gas inlet may be provided near the first end of the draft tube. In such instance, the at least one gas inlet supplies gas to the inside of the draft tube through at least one opening into the draft tube.

The draft tube further comprises an inlet for the reaction mixture at its first end. It will be appreciated that micro-organisms require reaction mixture and air (or gas), such as oxygen to produce carbon dioxide, to grow. Therefore, the bioreactor is designed to ensure a regulated liquid flow and at least one gas inside the reaction chamber and an outflow of used reaction mixture and excess gases from the reaction chamber. Furthermore, the bioreactor is designed to ensure proper mixing of the reaction mixture, i.e. mixing of at least one gas with the liquid phase in the reaction mixture. Furthermore, injection of gas into the reaction mixture results in a mixture of gas bubbles and the liquid phase of the reaction mixture (referred to as "gas-liquid mixture" hereafter). Optionally, the reaction mixture flows into the inlet for the reaction mixture at the first end on the draft tube from a source of fresh supply of the reaction mixture, optionally arranged outside the bioreactor, that stores reaction mixture. Alternatively, the reaction mixture flows into the inlet for the reaction mixture at the first end on the draft tube from the reaction mixture in the reaction chamber by means of circulation.

Optionally, the draft tube further comprises an impeller for mixing the reaction mixture, arranged inside the draft tube. The term "impeller" as used herein refers to a rotating device for moving liquid phase of the reaction mixture, by means of rotation of its blades. Specifically, the impeller increases the pressure and flow of liquid phase outwards from the centre of rotation, thereby increasing the efficiency of the liquid phase of the reaction mixture to mix with the gas in the draft tube. Optionally, the impeller is arranged closer to the first end of the draft tube than the at least one gas inlet. It will be appreciated that the impeller is arranged closer to the first end of the draft tube to receive a portion of the reaction mixture and ensure proper mixing of gases in liquid phase before the reaction mixture from the draft tube flows into the reaction chamber and mixes with the reaction mixture therein. Furthermore, the impeller is arranged to make the reaction mixture flow in a defined direction, i.e. downwards inside of the draft tube and upwards outside of the draft tube, specifically between the side wall of the draft tube and a wall of the reaction chamber, to ensure proper mixing of the reaction mixture with gases. Moreover, proper mixing of the reaction mixture is ensured by a combination of bioreactor mixing systems and gas injection systems, for example sparging systems. The rotation speed of the impeller can be for example 100-1000 rpm, such as 400-600 rpm. Optionally, the impeller is arranged with an engine, that rotates the impeller. In an embodiment, a pulley is arranged at a suspended end (outside the reaction chamber) of the agitation axle of the impeller. Furthermore, the pulley is coupled to a motor shaft of the engine by a belt drive, to provide rotational movement to the impeller. Moreover, the motor shaft of the engine acts as a driver and the agitation axle of the impeller acts as a driven. It will be appreciated that the belt drive transmits power at high efficiency (above 90%).

It will be appreciated that since the impeller is typically arranged closer to the first end of the draft tube, smaller gas bubbles that provide more surface area for the liquid phase of the reaction mixture for adhesion, move downwards towards the second end of the draft tube. Moreover, larger gas bubbles are more buoyant as compared to the smaller gas bubbles and therefore tend to rise up in the draft tube. However, the larger gas bubbles are broken down into smaller gas bubbles by the impeller for efficient mixing of the reaction mixture.

The draft tube further comprises an outlet for the reaction mixture at its second end. The draft tube regulates the flow of reaction mixture from the draft tube into the reaction chamber and balances out the shear and pressure forces throughout the reaction chamber. Notably, the gas-liquid mixture moves towards the second end of the draft tube and into the reaction chamber for further mixing with the rest of the reaction mixture in the reaction chamber. Specifically, the outlet for the reaction mixture at the second end of the draft tube enables supply of the gas-liquid mixture to the reaction mixture in the reaction chamber. Furthermore, the height $H_d$ of the draft tube plays an important role in avoiding cavitation as the draft tube encloses a part of the reaction mixture of the reaction chamber and avoids cavitation.

The bioreactor comprises at least one inlet for reaction medium. It will be appreciated that micro-organisms use the reaction mixture in order to grow. Therefore, the bioreactor is designed to ensure a regulated liquid flow and at least one gas inside the reaction chamber and an outflow of used reaction mixture and excess gases from the reaction chamber. Notably, the reaction medium is supplied to the at least one inlet for reaction medium from a source of reaction medium. The at least one inlet for reaction medium provides fresh reaction medium, comprising a sterile liquid phase with or without nutrients, to the reaction chamber. In an example, the reaction medium may be a Luria Broth medium. It will be appreciated that at a lag phase (i.e. a phase in the growth of micro-organism), the reaction chamber becomes saturated with the micro-organisms which use most of the energy, in terms of nutrients and gases from the reaction mixture and lower the efficiency of the bioreactor while increasing the operational cost of the bioreactor. Therefore, removal of grown micro-organisms is required to restore the operation of the bioreactor.

The bioreactor comprises at least one outlet for withdrawing medium with grown micro-organisms. Optionally, once the culture of micro-organisms has achieved an optimal growth, micro-organisms can be harvested from the reaction chamber. Optionally, the at least one outlet for withdrawing grown micro-organisms is arranged at the first end of the reaction chamber, i.e. at the top of the reaction chamber. Since the micro-organism growth is lighter as compared to the reaction mixture, the layer of grown micro-organisms may be harvested from the surface of the reaction mixture. Notably, the remaining volume of the reaction chamber, above the surface of the reaction mixture is filled with excess gas. In this regard, the at least one outlet for withdrawing medium with grown micro-organisms is used to withdraw medium with grown micro-organisms from the reactor chamber. Moreover, the at least one outlet for withdrawing medium with grown micro-organisms can also be used for removing, by means of venting, excess gas out of the reaction chamber.

The bioreactor further comprises at least one blade structure arranged inside the reaction chamber, surrounding the draft tube, wherein the at least one blade structure comprises a plurality of blades arranged at, at least one of an angle $\alpha_1$ with respect to a direction defined by the height of the reaction chamber, the angle $\alpha_1$ being 20-40°, or an angle $\alpha_2$ with respect to a direction defined by the height of the reaction chamber, the angle $\alpha_2$ being 320-340°. This is also called the first blade structure.

According to an embodiment, the bioreactor further comprises a second blade structure arranged inside the reaction chamber, surrounding the draft tube. The second blade structure is arranged at a distance $L_1$ from the first blade structure. In this case, the first blade structure comprises a plurality of blades arranged at an angle $\alpha_1$ with respect to a direction defined by the height of the reaction chamber, the angle $\alpha_1$ being 20-40°, and the second blade structure comprises a plurality of blades arranged at an angle $\alpha_2$ with respect to a direction defined by the height of the reaction chamber, the angle $\alpha_2$ being 320-340°. In the following explanations (as well as above), when "one blade structure" is mentioned, the explanations are valid for both the first and second blade structures. Furthermore, the bioreactor, especially if its dimensions are large, may comprise further blade structures (third, fourth, fifth etc.) arranged inside the reaction chamber and surrounding the draft tube. Most preferably the angles of the blades of the blade structures are such that the angles of two consecutive blade structures are different, so as to increase the movement of the reaction mixture within the reaction chamber.

Furthermore, in such an instance the first, second and further blade structures may be arranged at same or different distances. Optionally, the distance $L_1$ between the first blade structure and the second blade structure may be about 5-25% of the inner height $H_r$ of the reaction chamber. The same applies independently for any other distance between two blade structures. For example, the distance may be from 5, 6, 7, 8, 9, 10, 12, 15, 17 or 20% up to 6, 7, 8, 9, 10, 12, 15, 17, 20, 22 or 25% of the inner height $H_r$ of the reaction chamber. When more than one blade structure is used, they are typically arranged at a distance from one another, wherein the distance between two sets of blade structures can be the same or different.

The angle $\alpha_1$ can be for example from 20, 22, 24, 26, 28, 30, 32 or 34° up to or 22, 24, 26, 28, 30, 32, 34, 36, 38 or 40°. The angle $\alpha_2$ can be for example from 320, 322, 324, 326, 328, 330, 332 or 334° up to or 322, 324, 326, 328, 330, 332, 334, 336, 338 or 340°. The angles of different blade structures can be the same or different.

The at least one blade structure is arranged perpendicularly to the direction of height of the draft tube or the reaction chamber. Moreover, the at least one blade structure surrounding the draft tube supports the installation of the draft tube inside the reaction chamber, wherein the outer circumference of the at least one blade structure is attached to the side wall of the reaction chamber and the inner circumference is anchored to the side wall of draft tube, at corresponding parallel sites. Furthermore, the at least one blade structure surrounding the draft tube receives the gas-liquid mixture from the outlet for the reaction mixture at the second end of the draft tube. The at least one blade structure surrounding the draft tube further enables longer residence time for the gas-liquid mixture, and provides a higher concentration of gas available for the micro-organisms to grow.

The at least one blade structure comprises a plurality of blades. The plurality of blades may be arranged on a support arrangement of the at least one blade structure. The support arrangement of the at least one blade structure has a plurality of openings, arranged at an angle $\alpha$ with respect to the each of the at least one blade structure and/or with respect to a direction defined by the inner height of the reaction chamber or height of the draft tube (as the at least one blade structure is arranged perpendicularly to the direction of height of the draft tube). Moreover, the plurality of openings corresponds to the plurality of blades arranged on the support arrangement and allow the plurality of blades to be fixed into the openings. Alternatively, the plurality of blades may be arranged on the support arrangement by any other method known in the art, such as by welding.

The plurality of blades is arranged at an angle $\alpha_1$, the angle $\alpha_1$ being 20° to 40°, with respect to the direction defined by the height of the reaction chamber. For example, the angle $\alpha_1$ may be from 20°, 25°, 30° or 35° up to 25°, 30°, 35° or 40°. Alternatively, the plurality of blades is arranged at an angle $\alpha_2$, the angle $\alpha_2$ being 320° to 340°, with respect to the direction defined by the height of the reaction chamber. For example, the angle $\alpha_2$ may be from 320°, 325°, 330° or 335° up to 325°, 330°, 335° or 340°. In an example, the blades of the at least one blade structure are arranged at an angle 30° or at an angle 330° with respect to a direction defined by the height of the reaction chamber. It will be appreciated that if the angles $\alpha_1$ or $\alpha_2$ are 0°, then the blades do not alter the direction of the reaction mixture, also if the angles $\alpha_1$ or $\alpha_2$ are 90°, then the blades prohibit the movement of the reaction mixture, therefore, the angles $\alpha_1$ and $\alpha_2$ being 20° to 40° and 320° to 340° respectively, provide efficient flow of the reaction mixture throughout the reaction chamber and force the reaction mixture to change direction.

Notably, the angle of the blades depends on the speed of the impeller, wherein the angle of the blades is proportional to the speed of the impeller. In an example, if the impeller rotates with low speed, then the angle of the blades should be low, for example, if the speed of the impeller is 100 meters per second (m/s) then the angle of the blade may be 20° to allow the reaction mixture to pass through the blades without damaging the blades or any hindrance. In another example, if the speed of the impeller is 500 meters per second (m/s) then the angle of the blade may be 40° to allow the reaction mixture to pass through the blades while having an increased residence time for causing proper mixing of reaction mixture with gas. The term "residence time" as used herein refers to the duration of time which a matter spends in a bioreactor. In an example, the residence time of a gas bubble in the gas-liquid mixture may range from 10 to 30 minutes. It will be appreciated that a smaller gas bubble has higher surface area and therefore longer residence time as compared to a larger gas bubble. For example, a gas bubble of diameter 2 millimetres has a residence time of 20 minutes while a gas bubble having a diameter of 1 millimetre has a longer residence time of 30 minutes.

Optionally, at least one blade structure comprises 30 to 60 blades. For example, the number of blades in the at least one blade structure may be from 30, 35, 40, 45 or 55 blades up to 35, 40, 45, 50, 55 or 60 blades. If several blade structures are used, they may comprise the same or different number of blades. For example, the number of blades in a second blade structure may be from 30, 35, 40, 45 or 55 blades up to 35, 40, 45, 50, 55 or 60 blades. Moreover, each of the blades of the at least one blade structure is inclined at equal angles with respect to the direction defined by the height of the draft tube and/or reaction chamber, thus bringing an even distribution of gas-liquid mixture throughout the at least one blade structure. Furthermore, the at least one blade structure can be fabricated from three parts, each part comprising a fixed number of blades. Optionally, each part comprises 10-20 blades. For example, each part of the at least one blade structure may comprise from 10, 11, 12, 13, 14, 15, 16, 17, 18 or 19 blades up to 11, 12, 13, 14, 15, 16, 17, 18 or 20 blades. Again, if more than one blade structure is used, each of them may comprise one or more parts, and each part may comprise a suitable number of blades, such as from 10, 11, 12, 13, 14, 15, 16, 17, 18 or 19 blades up to 11, 12, 13, 14, 15, 16, 17, 18 or 20 blades. In an example, where each part comprises 14 blades, the at least one blade structure will have a total of 42 blades.

It will be appreciated that based on the height $H_d$ of the draft tube, the bioreactor may include a plurality of blade structures. For example, the bioreactor may include two, three or more blade structures, arranged inside the reaction chamber, surrounding the draft tube. Furthermore, in such an instance the plurality of blade structures may be arranged at a predefined distance apart from each other. Notably, the predefined distance between the plurality of blade structures may be same or different. For example, as mentioned above, one blade structure may be arranged at the distance $L_1$ from an adjacent blade structure, that is at a distance $L_2$ from another blade structure, and so on. Moreover, $L_1$ may be equal to or smaller or larger than $L_2$. Optionally, the distance $L_1$ between a blade structure and the adjacent blade structure may be about 5-25% of the inner height $H_r$ of the reaction chamber. The same applies independently for any other distance between any two blade structures. For example, the distance may be from 5, 6, 7, 8, 9, 10, 12, 15, 17 or 20% up to 6, 7, 8, 9, 10, 12, 15, 17, 20, 22 or 25% of the inner height $H_r$ of the reaction chamber.

In an embodiment, the first blade structure causes the gas-liquid mixture to flow in a clockwise direction and the second blade structure causes the gas-liquid mixture to flow in a counter-clockwise direction. The arrangement of the first blade structure and the second blade structure enables longer residence time for the gas-liquid mixture, thus enabling a higher concentration of gas in the gas-liquid mixture available for the micro-organisms to grow.

The bioreactor further comprises means for generating flow of the reaction mixture within the reaction chamber. Specifically, the means for generating flow of the reaction mixture within the reaction chamber is operable to direct the liquid flow from the at least one inlet for reaction medium to the draft tube and back into the reaction chamber.

Optionally, the means for generating flow of the reaction mixture within the reaction chamber is a pump and the draft tube comprises at least one internal blade structure arranged perpendicular to the direction of height of the draft tube. Furthermore, the internal blade structure comprises a plurality of blades arranged at an angle $\alpha_{d1}$ with respect to a direction defined by the height of the draft tube, the angle $\alpha_{d1}$ being 20-40°. Optionally, the pump is operable to direct the liquid flow into the reaction chamber by rotating the reaction mixture. More optionally, the pump receives the reaction mixture from the at least one inlet for reaction medium that provides fresh reaction medium to the draft tube where the impeller further directs the liquid flow downwards into the draft tube. When a pump is used, its power can be for example 0.1-5 kW, such as 0.3-0.8 kW.

Optionally, the draft tube comprises at least one internal blade structure arranged perpendicular to the direction of height of the draft tube, wherein the at least one internal blade structure comprises a plurality of blades arranged at an angle $\alpha_{d1}$ with respect to a direction defined by the height of the draft tube, the angle $\alpha_{d1}$ being 20° to 40°. Optionally, the plurality of blades is arranged on a support arrangement of the at least one internal blade structure. The support arrangement of the at least one internal blade structure may have a plurality of openings, arranged at an angle $\alpha$ with respect to the internal blade structure and/or with respect to a direction defined by the height of the draft tube. For example, the plurality of openings is arranged at an angle $\alpha_{d1}$ with respect to one of the at least one internal blade structure. Moreover, the plurality of openings corresponds to the plurality of blades arranged on the support arrangement and allow the plurality of blades to be fixed into the openings. Alternatively, the plurality of blades may be arranged on the support arrangement by any other method known in the art, such as by welding. The plurality of blades of the at least one internal blade structure is arranged at an angle $\alpha_{d1}$ with respect to a direction defined by the height of the draft tube, the angle $\alpha_{d1}$ being 20° to 40°. For example, the angle $\alpha_{d1}$ may be from 20°, 25°, 30° or 35° up to 25°, 30°, 35° or 40°.

Furthermore, the at least one internal blade structure enhances proper mixing of gas and the liquid phase enclosed in the draft tube propelled via the impeller. The blades of the internal blade structure may be fixed at an angle $\alpha_{d1}$, which may be from 20°, 25°, 30° or 35° up to 25°, 30°, 35° or 40°. It will be appreciated that if the angle $\alpha_{d1}$ is 0°, then the blades do not alter the direction of the reaction mixture as directed by the impeller. If the angle $\alpha d_1$ is 90°, then the blades prohibit the movement of the reaction mixture as directed by the impeller, therefore, the angle $\alpha_{d1}$ being 20° to 40° provides efficient mixing of gas bubbles into the liquid phase and consequently flow of the reaction mixture throughout the reaction chamber.

Optionally, at least one internal blade structure comprises independently 30 to 60 blades. For example, the number of blades in the at least one internal blade structure may be from 30, 35, 40, 45 or 55 blades up to 35, 40, 45, 50, 55 or 60 blades. Moreover, each of the blades of the at least one internal blade structure is inclined at equal angles with respect to the direction defined by the height of the draft tube, thus bringing an even distribution of gas-liquid mixture throughout the at least one internal blade structure. Furthermore, the at least one internal blade structure can be fabricated from three parts, each part comprising a fixed number of blades. Optionally, each part comprises 10-20 blades. For example, each part of the at least one internal blade structure may comprise from 10, 11, 12, 13, 14, 15, 16, 17, 18 or 19 blades up to 11, 12, 13, 14, 15, 16, 17, 18 or 20 blades. In an example, where each part comprises 14 blades, the at least one internal blade structure will have a total of 42 blades.

Optionally, the draft tube comprises two internal blade structures arranged at a distance from each other, and the blades of the two internal blade structures are arranged at different angles with respect to the direction defined by the height of the draft tube. Optionally, the two internal blade structures are arranged around the agitation axle of the impeller, at a distance $L_{d1}$ from each other. Optionally, the distance $L_{d1}$ may be about 5-25% of the height $H_d$ of the draft tube. Furthermore, the plurality of blades of the two internal blade structures are arranged at different angles with respect to the direction defined by the height of the draft tube and with respect to the previous blade structure. For example, if the plurality of blades of one of two internal blade structures has an angle 30°, then the plurality of blades of the second of the two internal blade structures has an angle 20° with respect to the direction defined by the height of the draft tube.

Optionally, the draft tube comprises three or more internal blade structures and the blades of each adjacent internal blade structures are arranged at different angles with respect to the direction defined by the height of the draft tube. The three or more internal blade structures are thus arranged around the agitation axle of the impeller at a distance $L_{d1}$ from each other. Optionally, the distance $L_{d1}$ may be about 5-25% of the height $H_d$ of the draft tube. When three or more internal blade structures are used, they are typically arranged at a distance from one another, wherein the distance between two consecutive blade structures can be the same or different. Furthermore, the blades of the three or more internal blade structures are arranged at different angles with respect to the direction defined by the height of the draft tube and with respect to the previous internal blade structure. For example, if the blades of one of three or more internal blade structures has an angle 30° then the blades of the second internal blade structure may have an angle 20° and the blades of the third internal blade structure may have an angle 10° (or again 30°, it being preferred that two consecutive internal blade structures have a different angle) with respect to the direction defined by the height of the draft tube, and so forth.

Notably, an arrangement of the two or three or more internal blade structures, arranged at different angles with respect to the direction defined by the height of the draft tube and with respect to the previous internal blade structure, causes the gas-liquid mixture to flow in different directions while passing through the two or three or more internal blade structures, consequently enabling longer residence time for the gas-liquid mixture, and enabling a higher concentration of gas in the gas-liquid mixture available for the microorganisms to grow.

Optionally, the at least one gas inlet, optionally provided on the side wall of the draft tube, is arranged closer to the second end of the draft tube than at least one internal blade structure. In an embodiment, the at least one gas inlet provided on the side wall of the draft tube is arranged between two internal blade structures, when two internal blade structures are used. It will be appreciated that the at least one gas inlet is arranged below the impeller and in between the two internal blade structures enable ejecting gas bubbles into the liquid phase of the reaction mixture enclosed by the draft tube for proper mixing therein. Furthermore, arranging the at least one gas inlet closer to the second end of the draft tube ensures flow of the gas bubbles in the opposite direction of the flow of the liquid as directed by the impeller, i.e. upwards the draft tube. Notably, the said arrangement ensures increased residence time and a distributed flow of the gas-liquid mixture throughout the reaction chamber by the at least one internal blade structure.

In an embodiment, apart from the pump and the draft tube comprising at least one internal blade structure arranged perpendicular to the direction of height of the draft tube, the impeller and the at least one blade structure, arranged inside the reaction chamber surrounding the draft tube, also generates flow of the reaction mixture within the reaction chamber. As mentioned before, the impeller is arranged to make the reaction mixture or gas-liquid mixture flow, in a defined direction, i.e. for example downwards inside of the draft tube and upwards outside of the draft tube, specifically between the side wall of the draft tube and a wall of the reaction chamber. The gas-liquid mixture flows via the at least one internal blade structure arranged perpendicular to the direction of height of the draft tube. Specifically, the at least one internal blade structure is arranged to alter the direction of movement of the gas-liquid mixture in order to increase the residence time and also to evenly distribute the gas bubbles throughout the reaction chamber in a more efficient manner. More specifically, the at least one internal blade structure and the at least one blade structure, arranged inside the reaction chamber surrounding the draft tube, are provided such that the adjacent blade structures direct the gas-liquid mixture to flow in a different direction, preferably opposite direction or a direction at an angle of about 90° compared to the previous direction, as compared to the previous one. It will be appreciated that the impeller and plurality of blade structures are arranged to cause the fluid to move in clockwise and/or counter-clockwise direction depending on blade directions on each of the three elements, the impeller, the at least one internal blade structure, and the at least one blade structure, arranged inside the reaction chamber surrounding the draft tube.

Optionally, the bioreactor further comprises a circulation unit for circulating, from the reaction chamber into the draft tube, at least one of gas inside the reaction chamber or reaction mixture inside the reaction chamber. Beneficially, the circulation unit provides an endless supply of at least one of gas inside the reaction chamber or reaction mixture inside the reaction chamber. Additionally, the circulation unit makes the bioreactor more energy efficient and cost-effective. Optionally, the circulation unit is installed outside the bioreactor. Alternatively, the circulation unit may be provided partly inside the bioreactor and partly outside the bioreactor (namely, "internal circulation unit"). In an example, the circulation unit increases retention time of accumulation of gases with the reaction mixture with the same amount of gases.

It will be appreciated that internal circulation unit must ensure substantial circulation of the at least one of gas inside the reaction chamber and reaction mixture inside the reaction chamber, especially in continuous culture of the bioreactor. It will be appreciated that the circulation unit may be operated using electricity, a pump, an ejector structure, a motor, and so forth.

In an implementation, the circulation unit is implemented by way of a gas pump. In such implementation, the circulation unit circulates, from the reaction chamber into the draft tube, gas inside the reaction chamber. It will be appreciated that gas inside the reaction chamber refers to the gas that gets free from the reaction mixture and not the gas still inside the reaction mixture. Optionally, the fresh gas inlet and the recycled gas inlet are provided on the side wall of the draft tube. It will be appreciated that the fresh gas inlet and the recycled gas inlet are preferably diametrically opposite.

The bioreactor may comprise a turbine connected to an axle, which axle is connected to an agitation shaft, for circulation of gas. According to another embodiment, the bioreactor comprises an external pump for circulation of gas.

In another implementation, the circulation unit is thus implemented by way of a turbine, such as a self-aspirating aerator. In such implementation, the circulation unit circulates, from the reaction chamber into the draft tube, gas inside the reaction chamber. Optionally, the turbine is provided below the first end of the reaction chamber (i.e. in the remaining volume), i.e. where excess gases are collected. The turbine may comprise curved blades and rotate at a specific speed around its central axis, or the hollow agitation axle. As the turbine rotates, it produces a centrifugal force that creates a low-pressure area inside its inner chamber (at a centre of the blades), thereby eliminating the need for an additional pressure input. The creation of such low-pressure results in suction of the gas inside a hollow agitation axle, that leads into the hollow agitation axle of the impeller, and pushing the collected gas therein. Furthermore, optionally, when the circulation unit is implemented by way of the turbine, the at least one gas inlet is provided on the first end of the reaction chamber and into the turbine. The turbine collects the fresh and excess (or recycled) gas and introduce it together in the draft tube by means of the agitation axle of the impeller. It will be appreciated that the agitation axle of the impeller comprises holes or openings for providing the fresh and recycled gas to the draft tube. Optionally, the openings in the agitation axle of the impeller may be provided with spargers for sparging small gas bubbles in the liquid phase of the reaction mixture in the draft tube. Notably, the turbine may vary in its specifications based on the density and viscosity of the reaction mixture. The turbine may be fabricated from stainless steel (for example type 304, 316 or 316 L), a plastics material and/or a combination thereof. Beneficially, in such implementation, where the circulation unit employs the turbine, less spargers will be needed, thereby reducing the cost of the system. Additionally, beneficially, such implementation does not result in an increase in the temperature of the reaction mixture.

In yet another implementation, the circulation unit is implemented by way of a liquid circulation pump attached to a common ejector structure. The common ejector structure includes a gas suction and a nozzle. The bioreactor may thus comprise an ejector structure connected to the at least one gas inlet. It will be appreciated that the liquid circulation pump circulates reaction mixture inside the reaction chamber by means of the nozzle of the common ejector structure and the gas suction of the common ejector structure enables circulation of the gas inside the reaction chamber. Optionally, the liquid circulation pump is provided outside the bioreactor and the common ejector structure is provided at the first end of the draft tube. Moreover, at least one gas inlet for supplying fresh gas into the draft tube may be provided on the side wall of the draft tube. In one embodiment, by way of such implementation, most of the mixing the reaction mixture with at least one gas is achieved by the liquid circulation pump and the common ejector structure. Therefore, installing an impeller in the draft tube may be avoided, thereby making the system more cost-effective.

Optionally, the bioreactor further comprises at least one sensor. The at least one sensor in operation determines at least one growth parameter describing the growth conditions, such as foam formation, a temperature, a liquid flow, a gas flow, a gas level and/or a liquid level within the reaction chamber for the growth of micro-organisms. The at least one sensor may be selected from a group consisting of a foam forming sensor, a temperature sensor, a liquid flow sensor, a gas flow sensor, a gas level sensor and a liquid level sensor. Optionally, the at least one sensor may also include a pH sensor and a biomass sensor. The gas level sensor may determine in operation relative concentrations of at least two of carbon dioxide gas, oxygen gas, nitrogen gas, methane gas, sulphur dioxide gas, carbon monoxide gas and a mixture of gases within the reaction chamber. The foam forming sensor determines in operation the foam formation within the reaction chamber. The temperature sensor, the pH sensor and the biomass sensor determine in operation the temperature, the pH and the biomass within the reaction chamber respectively. The liquid flow control sensor and the gas flow control sensor determine in operation the rate of liquid flow and gas flow within the reaction chamber respectively. The liquid level sensor determines in operation the level of liquid within the reaction chamber.

Optionally, the at least one sensor is communicably coupled to at least one regulator. The at least one regulator in operation regulates the at least one growth parameter describing the growth conditions, such as foam formation, gas level, temperature, pH, biomass and liquid flow and gas and liquid level within the reaction chamber for the growth of micro-organisms. The at least one regulator is selected from a group comprising a gas level regulator, a temperature regulator, a liquid flow control regulator, a gas flow control regulator, a liquid level regulator, a pH regulator and a biomass regulator. The gas level regulator may regulate in operation the relative concentrations of at least two of carbon dioxide gas, oxygen gas, nitrogen gas, methane gas, sulphur dioxide gas, carbon monoxide gas and a mixture of gases within the reaction chamber, in order to attain a balance of gases within the reaction chamber suitable for the growth of micro-organisms. The temperature regulator, the pH regulator and the biomass regulator regulate in operation the temperature, the pH and the biomass within the reaction chamber respectively. The liquid flow control regulator and the gas flow control regulator regulate in operation the rate of liquid flow and gas within the reaction chamber respectively, such that an increased residence time is achieved for proper mixing of the two phases, the liquid and the gas phases. The liquid level regulator regulates in operation the level of liquid within the reaction chamber.

Optionally, the sensor and the regulator are communicably coupled in operation to a controller. The controller in operation obtains information related to the at least one of growth parameter required for the growth of micro-organisms. The controller receives at least one sensor signal describing the growth conditions from at least one sensor, compares the obtained at least one of growth parameter with the received at least one sensor signal, to generate at least one instruction for the at least one regulator for regulation of the at least one growth parameter within the reaction chamber for growing micro-organisms. The regulator further receives in operation the instruction from the controller and regulates the at least one growth parameter by adjusting the at least one growth parameter within the reaction chamber. Optionally, the at least one growth parameter describing growth conditions that are optimal for growing micro-organisms is obtained from a database, wherein the database is communicably coupled to the controller. Furthermore, the database relates to an organized body of digital information regardless of a manner in which the data or the organized body thereof is represented. More optionally, the database may be hardware, software, firmware and/or any combination thereof. For example, the organized body of digital information may be in a form of a table, a map, a grid, a packet, a datagram, a file, a document, a list or in any other form. The database may include any data storage software and required system. More optionally, the controller is communicatively coupled to the database via a communication network. In an example, the communication network includes but not limited to, a cellular network, short range radio (for example, such as Bluetooth®), Internet, a wireless local area network, and an Infrared Local Area Network, or any combination thereof.

Furthermore, the at least one sensor in operation determines the at least one growth parameter describing growth conditions continuously or intermittently. Beneficially, the at least one sensor is an automated sensor arrangement configured to determine a slight change in the at least one growth parameter describing growth conditions within the reaction chamber continuously throughout the production time, or at predefined time durations, such as at time durations in a gap of at least one of 30 minutes, 1 hour, 2 hours, 1 day, and so forth. Moreover, such changes in at least one growth parameter describing growth conditions determined by the at least one sensor are received by the controller continuously or at predefined time durations of determination of such changes. Furthermore, the controller is operable to provide the at least one instruction to the at least one regulator for regulating the at least one growth parameter within the reaction chamber for growing micro-organisms. Optionally, the controller in operation provides the at least one instruction to the regulator continuously or intermittently. Specifically, the controller is operable to provide the at least one instruction to the regulator to regulate the at least one growth parameter within the reaction chamber continuously or at predefined time durations receiving the at least one instruction from the controller.

In an embodiment, the regulated growth conditions within the reaction chamber may include a concentration of hydrogen in inlet gas in a range of 25% to 85%, optionally in a range of 40% to 80%, and more optionally in a range of 55% to 70%, concentration of carbon dioxide in inlet gas in a range of 5% to 50%, optionally in a range of 10% to 40%, and more optionally in a range of 15% to 25%, concentration of oxygen in inlet gas in a range of 1% to 25%, optionally in a range of 5% to 20%, and more optionally in a range of 5% to 15%, temperature in a range of 10° C. to 75° C., optionally in a range of 25° C. to 45° C., pH in a range of 3° C. to 10° C., optionally in a range of 5.5° C. to 7.5° C., biomass in a range of 0.5 to 60 g/L (cell dry weight), optionally in a range of 20 to 40 g/L, flowrate of reaction mixture in a range of 0.005 L/h per litre of reaction chamber volume to 0.5 L/h per litre of reaction chamber volume, optionally in a range of 0.01 L/h per litre of reaction chamber volume to 0.1 L/h per litre of reaction chamber volume, flowrate of inlet gas in a range of 50 mL/min per litre of reaction chamber volume to 2000 mL/min per litre of reaction chamber volume, optionally in a range of 60 mL/min per litre of reaction chamber volume to 200 mL/min per litre of reaction chamber volume, and the liquid level in a range of 70% to 100%, optionally in a range of 80% to 90%, within the reaction chamber.

Optionally, the gas may be heated or cooled in a gas supply unit to an optimal temperature range for the growth of micro-organisms, before transferring the gas into the at least one gas inlet. Alternatively, the gas may be heated or cooled by providing a water jacket around the pipe and supplying hot or cold water therein.

Optionally, the micro-organism culture process may be any one of a continuous culture process or a batch-type culture process. The continuous culture process requires addition of reaction mixture and/or gas into the bioreactor and removal of the grown micro-organisms and excess gases from the bioreactor at the same time. The batch-type culture process requires making and running one batch for a pre-defined period of time, without any addition of reaction mixture and/or gas into the bioreactor and removal of the grown micro-organisms and excess gases from the bioreactor after the process is finished (or has reached a pre-defined target).

In another aspect, an embodiment of the present disclosure provides a method for growing micro-organisms, comprising providing a reaction mixture comprising a reaction medium and micro-organisms;
providing at least one gas;
mixing the at least one gas with the reaction medium by flowing the at least one gas and the reaction medium in at least two directions; and
withdrawing grown micro-organisms and/or excess gas.

DETAILED DESCRIPTION OF THE DRAWINGS

Referring to FIG. 1, there is shown a schematic illustration of a bioreactor 100 for growing micro-organisms, in accordance with an embodiment of the present disclosure, as seen from the outside. The bioreactor 100 comprises a reaction chamber 102, gas inlets 104, 106 and 108 and an outlet 110 for withdrawal of grown micro-organisms. The bioreactor 100 further comprises a sensor 112.

Figure 2:
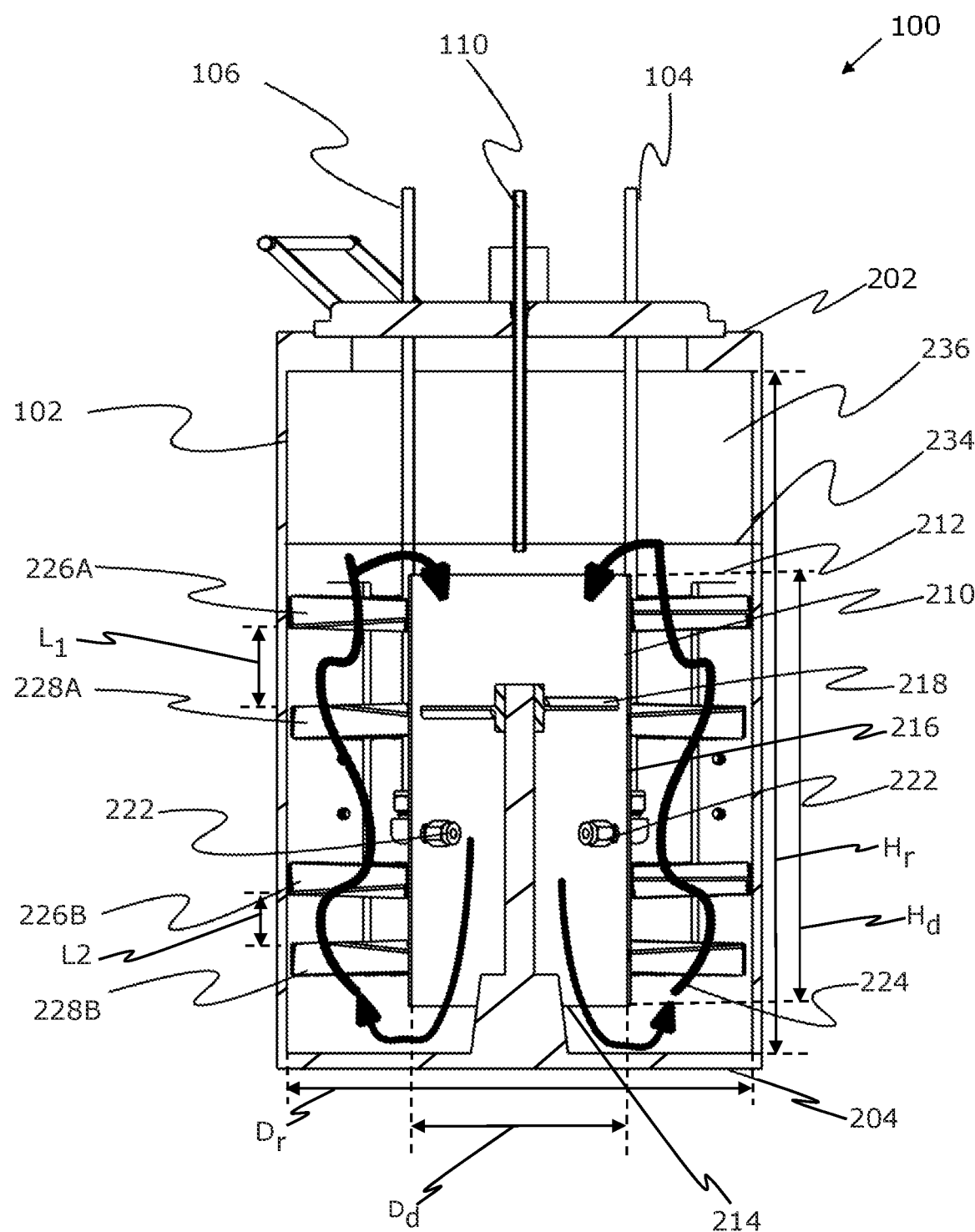
FIG. 2 is a schematic illustration of a cross-sectional view of a bioreactor along an axis X-X', in accordance with an embodiment of the present disclosure.

Referring to FIG. 2, there is shown a schematic illustration of a cross-sectional view of the bioreactor 100 of FIG. 1 along an axis X-X', in accordance with an embodiment of the present disclosure. As shown, the reaction chamber 102 includes an inner diameter $D_r$, a first end 202, a second end 204, and an inner height $H_r$ defined by a distance between the first end 202 and the second end 204. The bioreactor 100 includes a draft tube 210, arranged inside the reaction chamber 102, having a first end 212, a second end 214 and a side wall 216 connecting the first end 212 to the second end 214. The draft tube 210 has an inner diameter $D_d$, a height $H_d$ defined by the distance between the first end 212 and the second end 214, at least one gas inlet 104 and 106, an inlet for the reaction mixture at its first end 212 (open top) and an outlet for the reaction mixture at its second end 214 (open bottom). The at least one gas inlet 104, 106 comprises a nozzle 222 at the end, on the side wall 216, that opens into the draft tube 210. Moreover, the draft tube 210 further comprises an impeller 218 for mixing the reaction mixture, arranged inside the draft tube 210.

The reaction chamber 102, as shown in FIG. 2, also has means (not shown) for generating a flow (shown with arrows 224) of the reaction mixture within the reaction chamber 102. The reaction chamber 102 also includes a first blade structure 226A, 226B and a second blade structure 228A, 228B arranged inside the reaction chamber and surrounding the draft tube. Furthermore, the first blade structure 226A is arranged at a distance $L_1$ from the second blade structure 228A, and the first blade structure 226B is arranged at a distance $L_2$ from the second blade structure 228B. Furthermore, a rise level 234 of the reaction mixture and remaining volume 236 filled with evolved gases is shown in the reaction chamber 102. The remaining volume 236 is located between the first end 202 of the reaction chamber 102 and the rise level 234 of the reaction mixture inside the reaction chamber 102.

Figure 3:
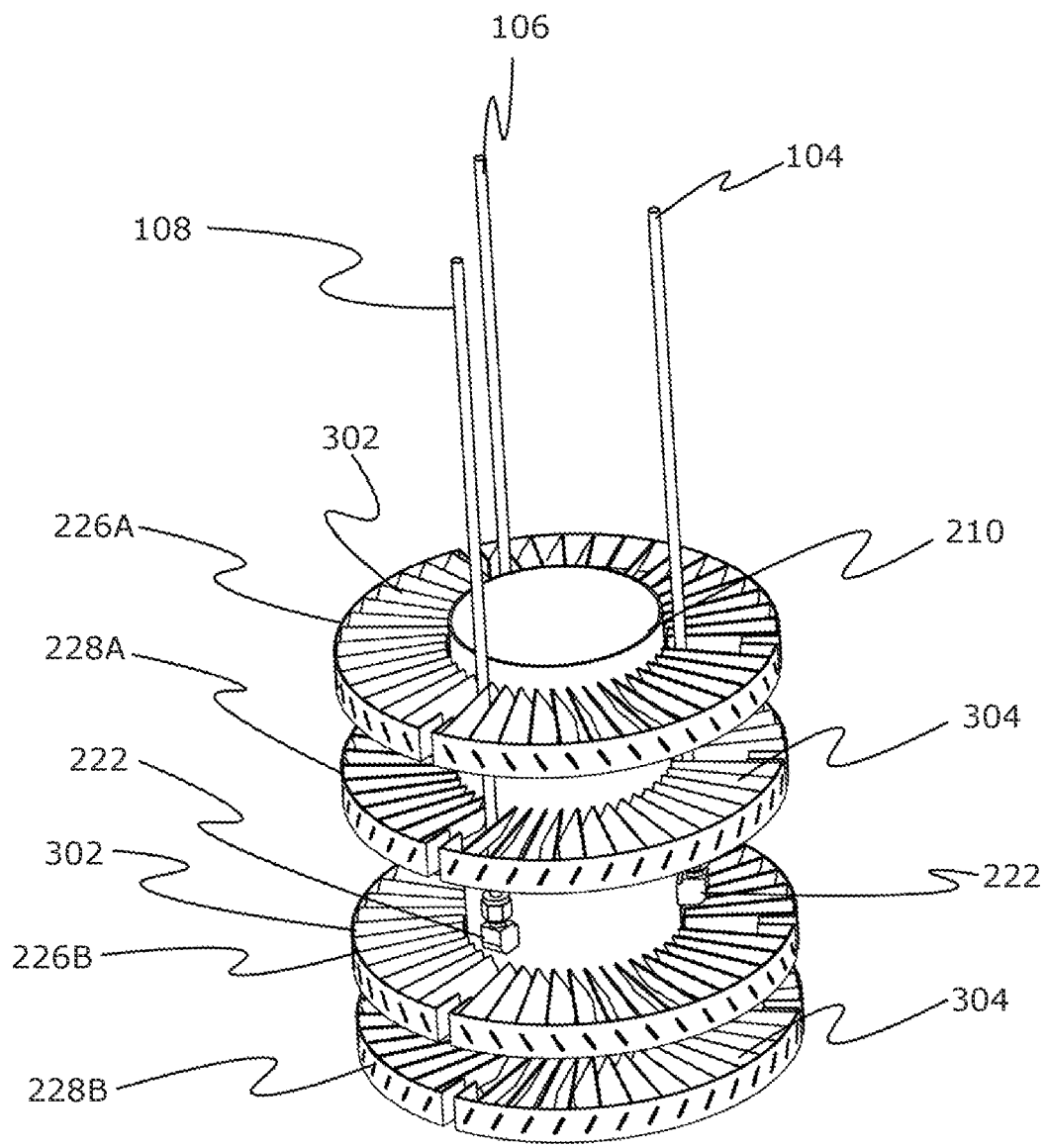
FIG. 3 is a schematic illustration of a draft tube, surrounded by at least one blade structure, in accordance with an embodiment of the present disclosure.

Referring to FIG. 3, there is shown a schematic illustration of the draft tube 210, surrounded by the first blade structure 226A, 226B and the second blade structure 228A, 228B, in accordance with an embodiment of the present disclosure. As shown, the first blade structure 226A, 226B comprises a first blade type 302 having a plurality of blades. Furthermore, the second blade structure 228A, 228B comprises a second blade type 304 having a plurality of blades. The different blade structures are arranged in alternate order. The FIG. 3 also shows the gas inlets 104, 106 and 108, draft tube 210 and nozzles 222.

Figure 4:
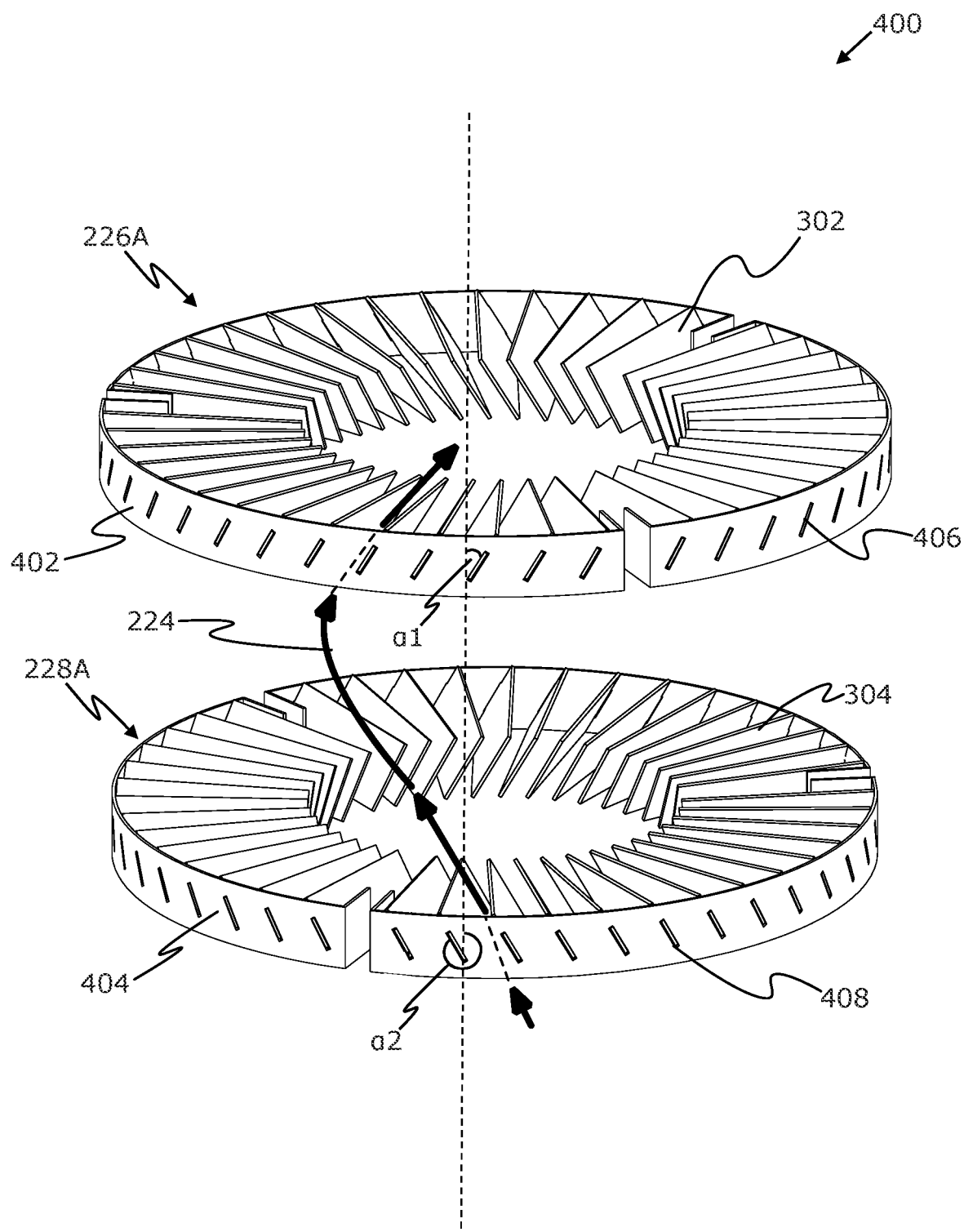
FIG. 4 is a schematic illustration of a first blade structure and a second blade structure, in accordance with an embodiment of the present disclosure.

Referring to FIG. 4, there is shown a schematic illustration of the first blade structure 226A and the second blade structure 228A, in accordance with an embodiment of the present disclosure. As shown, the first blade structure 226A comprises a first blade type 302 having a plurality of blades arranged at an angle $\alpha_1$ with respect to the direction defined by the height $H_r$ of the reaction chamber. Furthermore, the angle $\alpha_1$ is 33° with respect to the direction defined by the height $H_r$. Additionally, the second blade structure 228A comprises a second blade type 304 having a plurality of blades arranged at an angle $\alpha_2$ with respect to the direction defined by the height $H_r$ of the reaction chamber 102. Furthermore, the angle $\alpha_2$ is 327° with respect to the direction defined by the height $H_r$. Moreover, the first blade structure 226A and the second blade structure 228A are arranged on supports 402 and 404, wherein each blade is attached to an opening, such as 406 and 408. Furthermore, the first blade structure 226A and the second blade structure 228A direct the flow of the reaction mixture as illustrated with the arrow 224.

Figure 5:
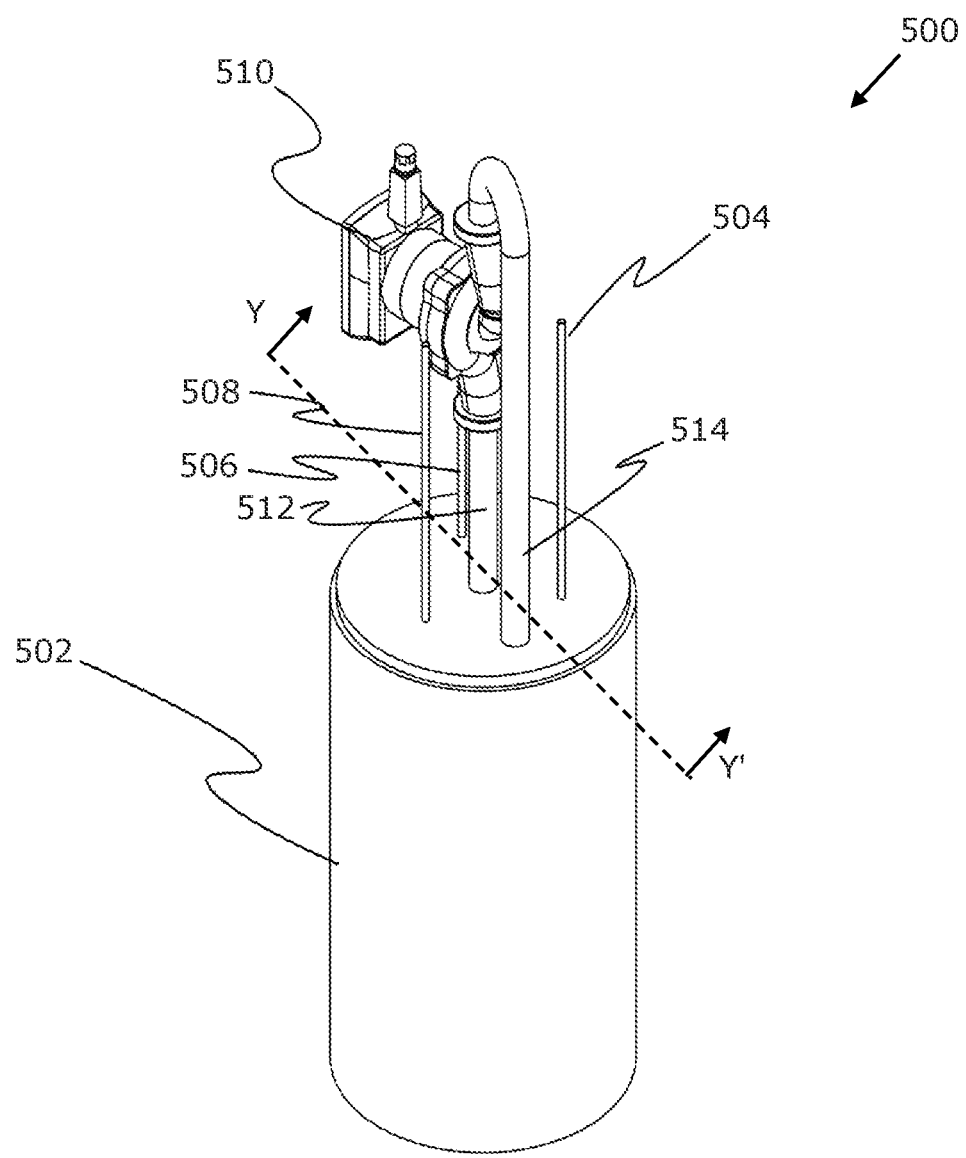
FIG. 5 is a schematic illustration of an exemplary implementation of a bioreactor for growing micro-organisms, in accordance with another embodiment of the present disclosure.

Referring to FIG. 5, there is shown a schematic illustration of an exemplary implementation of a bioreactor 500 for growing micro-organisms, in accordance with another embodiment of the present disclosure. As shown, the bioreactor 500 has a reaction chamber 502 and gas inlets 504, 506 and 508 for providing gases. The bioreactor 500 also has a pump 510 operable to circulate the reaction mixture into the reaction chamber 502 via a liquid inlet 512 and out from the reaction chamber 502 via an outlet 514.

Figure 6:
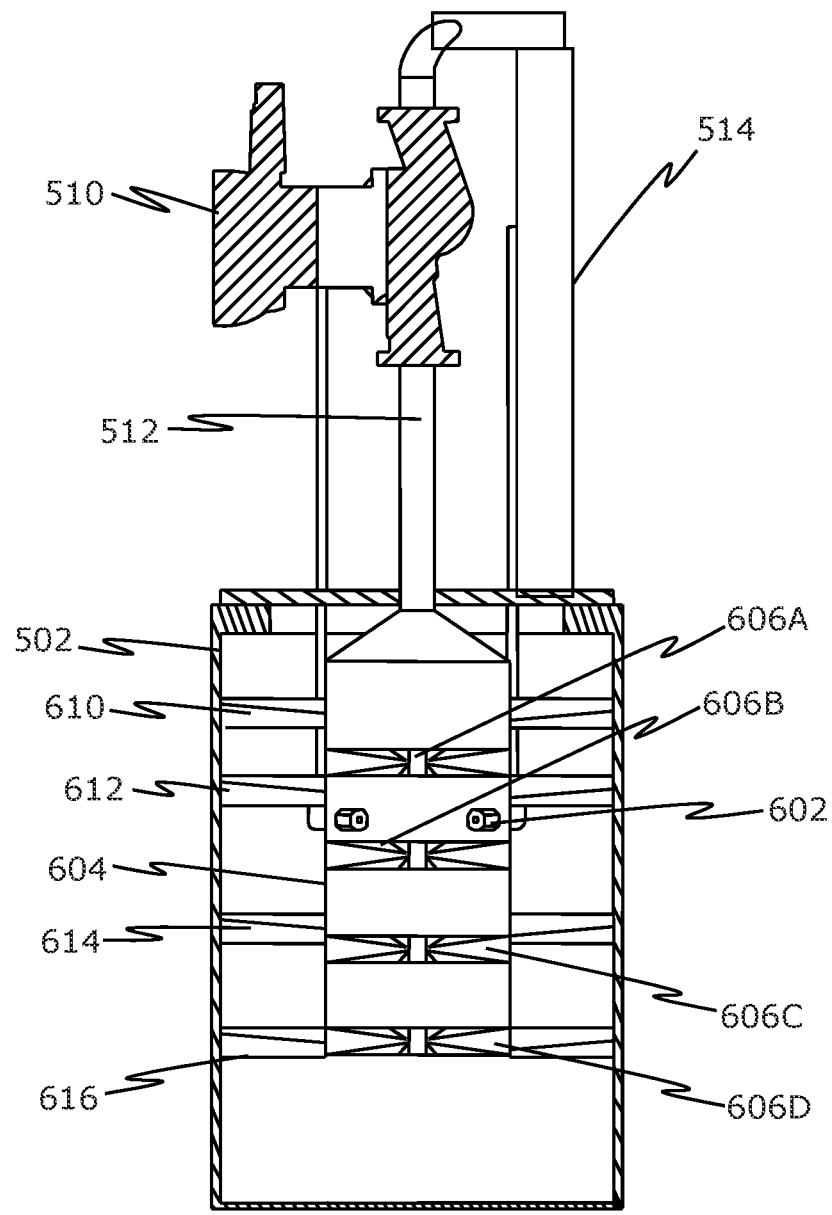
FIG. 6 is a schematic illustration of a cross-sectional view of the bioreactor along an axis Y-Y', in accordance with an embodiment of the present disclosure.

Referring to FIG. 6, there is shown a schematic illustration of a cross-sectional view of the bioreactor 500 of FIG. 5 along an axis Y-Y', in accordance with an embodiment of the present disclosure. As shown, the bioreactor 500 includes a reaction chamber 502, a liquid inlet 512 and an outlet 514 as well as inlets 602, a draft tube 604 comprising a set of internal blade structures 606A, 606B, 606C, 606D and a set of external blade structures 610, 612, 614, 616. The pump 510 circulates the reaction mixture within the set of internal blade structures 606A, 606B, 606C, 606D and the set of external blade structures 610, 612, 614, 616.

Figure 7:
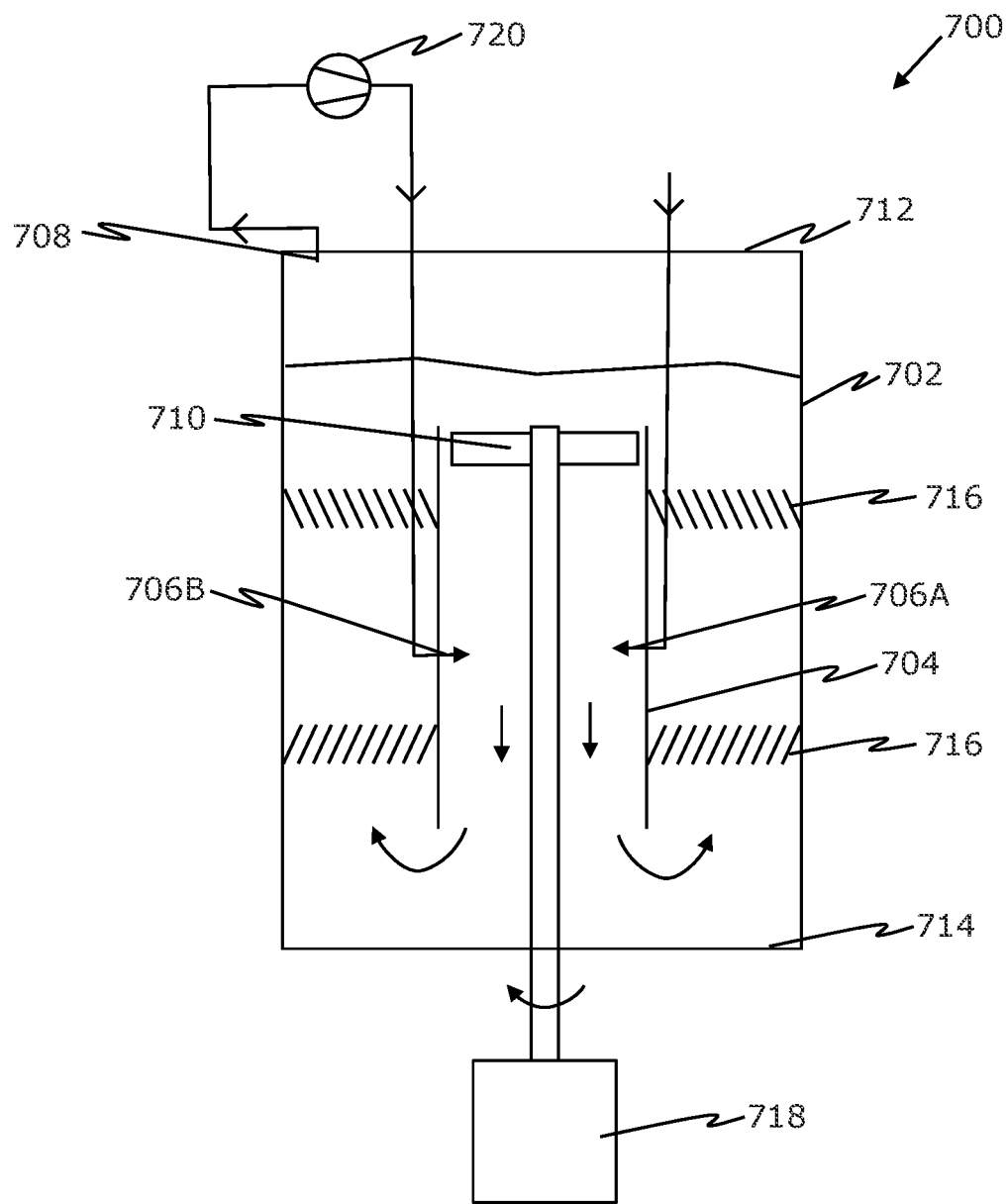
FIGS. 7, 8A-B and 9 are schematic illustrations of various exemplary implementations of a bioreactor for growing micro-organisms, in accordance with various embodiments of the present disclosure.

Referring to FIG. 7, there is shown a schematic illustration of an exemplary implementation of a bioreactor 700 for growing micro-organisms, in accordance with another embodiment of the present disclosure. The bioreactor 700 includes a reaction chamber 702. The reaction chamber 702 includes a draft tube 704, gas inlets 706A and 706B, a gas outlet 708, and an impeller 710. The reaction chamber 702 also includes a first end 712 and a second end 714. The reaction chamber 702 further includes blade structures 716 arranged inside the reaction chamber 702 and surrounding the draft tube 704. The bioreactor 700 also includes a motor shaft 718 coupled to the impeller 712. Furthermore, the motor shaft 718 rotates the impeller 712. The bioreactor 700 further includes a pump 720 arranged outside the reaction chamber 702 for circulating gases from the gas outlet 710 to the draft tube 704 through the gas inlet 708.

Figure 8A:
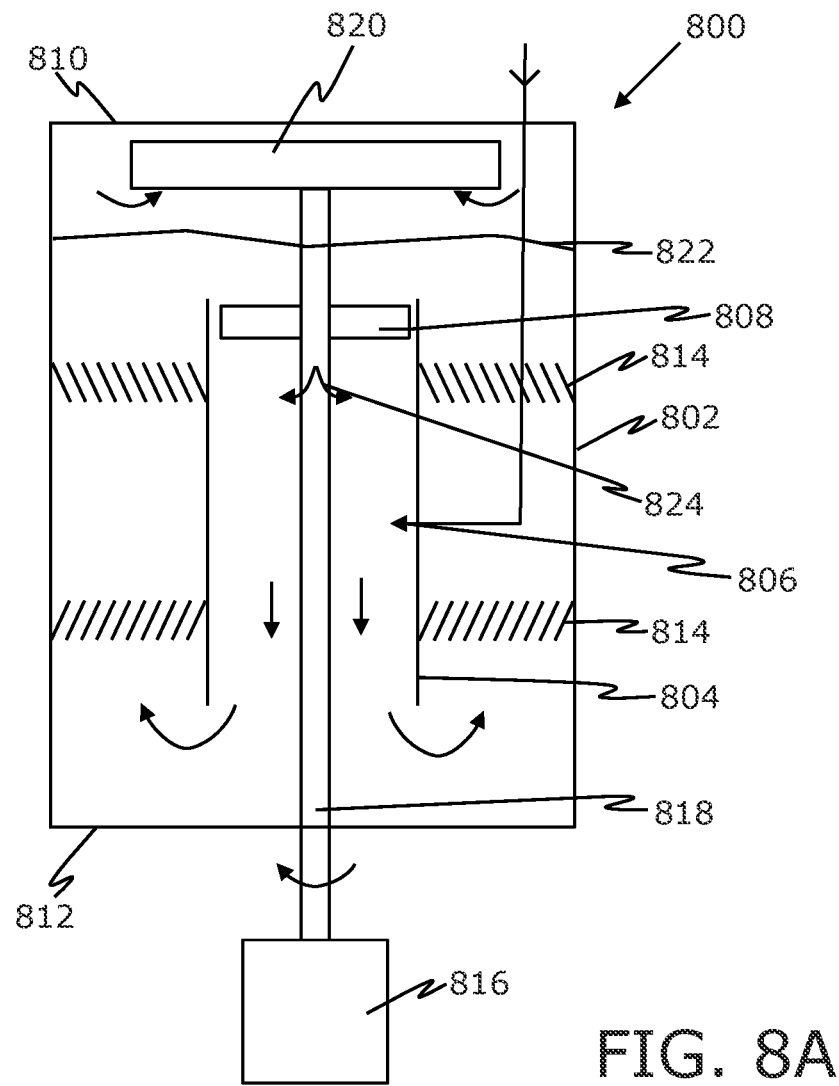
Figure 8B:
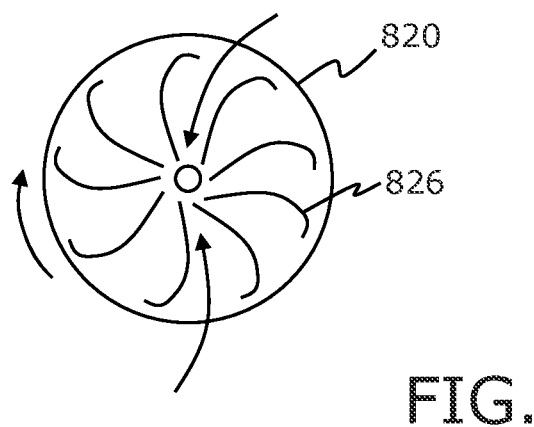

Referring to FIGS. 8A and 8B, there is shown a schematic illustration of an exemplary implementation of a bioreactor 800 for growing micro-organisms, in accordance with another embodiment of the present disclosure. The bioreactor 800 includes a reaction chamber 802. The reaction chamber 802 includes a draft tube 804, a gas inlet 806, and an impeller 808. The reaction chamber 802 also includes a first end 810 and a second end 812. The reaction chamber 802 also include blade structure 814 arranged inside the reaction chamber 802 and surrounding the draft tube 804. The bioreactor 800 further includes a motor shaft 816 coupled to the impeller 808. Furthermore, the motor shaft 816 rotates a hollow agitation axle 818 of the impeller 808. The bioreactor 800 further includes a turbine 820, arranged above a rise level 820 of the reaction mixture, and coupled to the impeller 808 through the hollow agitation axle 818 and rotated by the motor shaft 816. Furthermore, the turbine 820 sucks the gases collected above the rise level 822 of the reaction mixture, and circulates the gases below the impeller 808 via outlets 824. As shown in FIG. 8B, a top view of the turbine 820, depicting movement of the surrounding gases around blades 826 of the turbine 820.

Figure 9:
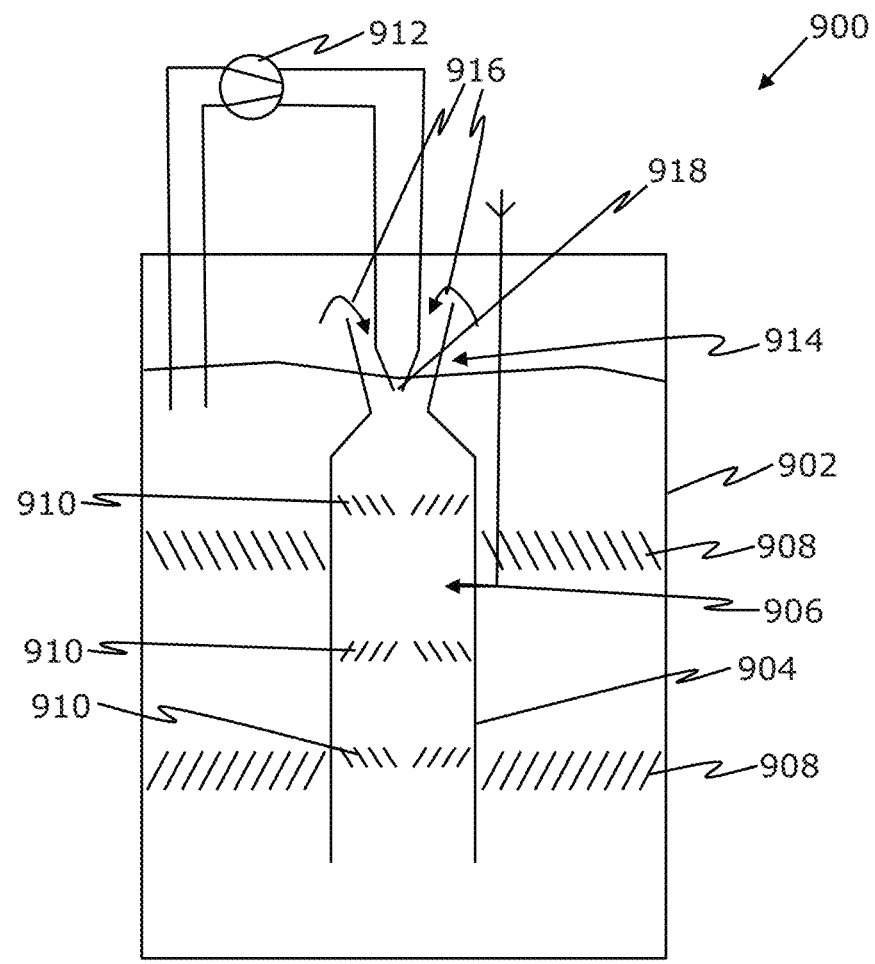

Referring to FIG. 9, there is shown a schematic illustration of an exemplary implementation of a bioreactor 900 for growing micro-organisms, in accordance with another embodiment of the present disclosure. The bioreactor 900 includes a reaction chamber 902. The reaction chamber 902 includes a draft tube 904, and a gas inlet 906. The reaction chamber 902 also include blade structure 908 arranged inside the reaction chamber 902 and surrounding the draft tube 904. Furthermore, the draft tube 904 includes internal blade structure 910 arranged inside the draft tube 904. The bioreactor 900 further includes a pump 912 arranged outside the reaction chamber 902 for circulating the reaction mixture from the reaction chamber 902 to the draft tube 904 through a common ejector structure 914. As shown, the common ejector structure 914 includes gas suction 916, and a nozzle 918. Furthermore, the reaction mixture is discharged from the nozzle 918 of the common ejector structure 914. Notably, a suction pressure is created at the gas suction 916 by the flow of the reaction mixture, resulting in intake of the surrounding gases to the common ejector structure 914. Therefore, a mixture of the gases and the reaction mixture is circulated to the draft tube 904.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A bioreactor for growing micro-organisms, comprising a reaction chamber for containing a reaction mixture comprising a reaction medium and micro-organisms, said reaction chamber having a first end, a second end, an inner height $H_r$ defined by the distance between an inner surface at the first end and an inner surface at the second end, and an inner diameter $D_r$, and comprising
    a draft tube arranged inside the reaction chamber, having
        a first end, a second end and a side wall connecting the first end to the second end,
        an inner diameter $D_d$, wherein $D_d$ is smaller than $D_r$,
        a height $H_d$ defined by the distance between the first end and the second end, wherein $H_d$ is smaller than $H_r$,
        at least one gas inlet,
        an inlet for the reaction mixture at the first end of the draft tube, and
        an outlet for the reaction mixture at the second end of the draft tube;
    means for generating flow of the reaction mixture within the reaction chamber;
    a first non-rotating blade structure attached to a side wall of the reaction chamber and surrounding the draft tube, wherein the first non-rotating blade structure comprises a plurality of blades fixed at, at least one of an angle $\alpha_1$ with respect to a direction defined by the height of the reaction chamber, the angle $\alpha_1$ being 20-40°, or an angle $\alpha_2$ with respect to a direction defined by the height of the reaction chamber, the angle $\alpha_2$ being 320-340°;

at least one inlet for the reaction medium; and at least one outlet for withdrawing the reaction mixture.

2. The bioreactor according to claim 1, further comprising a second non-rotating blade structure arranged inside the reaction chamber, surrounding the draft tube, the second non-rotating blade structure being arranged at a distance $L_1$ from the first non-rotating blade structure;

the first non-rotating blade structure comprising a plurality of blades arranged at an angle $\alpha$ with respect to a direction defined by the height of the reaction chamber, the angle $\alpha_1$ being 20-40°; and the second non-rotating blade structure comprising a plurality of blades arranged at an angle $\alpha_2$ with respect to a direction defined by the height of the reaction chamber, the angle $\alpha_2$ being 320-340°.

3. The bioreactor according to claim 1, wherein the bioreactor further comprises a circulation unit for circulating, from the reaction chamber into the draft tube, at least one of gas inside the reaction chamber and reaction mixture inside the reaction chamber.

4. The bioreactor according to claim 1, wherein the at least one gas inlet is provided on the side wall of the draft tube.

5. The bioreactor according to claim 1, wherein the at least one gas inlet comprises a nozzle comprising a number of openings for creating gas bubbles.

6. The bioreactor according to claim 1, wherein the at least one outlet for withdrawing the reaction mixture is arranged at the first end of the reaction chamber.

7. The bioreactor according to claim 1, wherein the means for generating flow of the reaction mixture comprises an impeller arranged inside the draft tube.

8. The bioreactor according to claim 7, wherein the impeller is arranged closer to the first end of the draft tube than the at least one gas inlet.

9. The bioreactor according to claim 1, further comprising a turbine connected to an axle, which axle is connected to an agitation shaft, for circulation of gas.

10. The bioreactor according to claim 1, further comprising an external pump for circulation of gas.

11. The bioreactor according to claim 1, wherein the means for generating flow of the reaction mixture within the reaction chamber is a pump and the draft tube comprises at least one internal blade structure arranged perpendicular to the direction of height of the draft tube, and the internal blade structure comprises a plurality of blades arranged at an angle $\alpha d1$ with respect to a direction defined by the height of the draft tube, the angle $\alpha d1$ being 20-40°.

12. The bioreactor according to claim 11, wherein the draft tube comprises two internal blade structures arranged at a distance from each other, and the blades of the two internal blade structures are arranged at different angles with respect to the direction defined by the height of the draft tube.

13. The bioreactor according to claim 11, wherein the draft tube comprises three or more internal blade structures and the blades of each adjacent internal blade structure are arranged at different angles with respect to the direction defined by the height of the draft tube.

14. The bioreactor according to claim 11, wherein the at least one gas inlet is arranged closer to the second end of the draft tube than the at least one internal blade structure.

15. The bioreactor according to claim 11, further comprising an ejector structure connected to the at least one gas inlet and/or the at least one inlet for the reaction medium.

16. The bioreactor according to claim 11, wherein the first non-rotating blade structure and the at least one internal blade structure comprise independently 30-60 blades.

17. The bioreactor according to claim 1, further comprising at least one sensor.

18. The bioreactor according to claim 17, wherein the at least one sensor is selected from a group consisting of a foam forming sensor, a temperature sensor, a liquid flow sensor, a gas flow sensor, a gas level sensor and a liquid level sensor.

19. The bioreactor of claim 1, wherein the first non-rotating blade structure further comprises a support arrangement, the plurality of blades being welded on the support arrangement.

20. The bioreactor of claim 1, wherein an outer circumference of the first non-rotating blade structure is attached to the side wall of the reaction chamber and the inner circumference is anchored to a side wall of the draft tube.

* * * * *